US008888703B2

(12) United States Patent
Abe et al.

(10) Patent No.: US 8,888,703 B2
(45) Date of Patent: Nov. 18, 2014

(54) ULTRASOUND IMAGING APPARATUS AND METHOD FOR PROCESSING IMAGE WITH MOTION TRACKING AND ERROR CORRECTION

(75) Inventors: Yasuhiko Abe, Otawara (JP); Tetsuya Kawagishi, Nasushiobara (JP); Katsuhisa Ishii, Osaka (JP)

(73) Assignees: Toshiba Medical Systems Corporation, Otawara-shi (JP); Kansai Electric Power Company, Inc., Osaka-shi (JP)

( * ) Notice: Subject to any disclaimer, the term of this patent is extended or adjusted under 35 U.S.C. 154(b) by 851 days.

(21) Appl. No.: 12/429,691

(22) Filed: Apr. 24, 2009

(65) Prior Publication Data

US 2009/0270732 A1 Oct. 29, 2009

(30) Foreign Application Priority Data

Apr. 25, 2008 (JP) .................. 2008-114854

(51) Int. Cl.
| | |
|---|---|
| A61B 8/00 | (2006.01) |
| G01S 7/52 | (2006.01) |
| A61B 8/13 | (2006.01) |
| G06T 7/20 | (2006.01) |
| A61B 8/08 | (2006.01) |

(52) U.S. Cl.
CPC ............... *A61B 8/13* (2013.01); *A61B 8/5284* (2013.01); *A61B 8/0891* (2013.01); *A61B 8/0883* (2013.01); *A61B 8/469* (2013.01); *A61B 8/483* (2013.01); *G01S 7/52071* (2013.01); *G01S 7/52042* (2013.01); *G06T 2207/10132* (2013.01); *A61B 8/463* (2013.01); *G06T 7/204* (2013.01); *G06T 2207/30048* (2013.01)
USPC ............ 600/443; 600/407; 382/128

(58) Field of Classification Search
USPC .......... 600/437, 443, 447, 450, 451, 454, 455
See application file for complete search history.

(56) References Cited

U.S. PATENT DOCUMENTS 5,913,824 A * 6/1999 Ogasawara et al. ........... 600/455
6,245,017 B1 * 6/2001 Hashimoto et al. ........... 600/447
(Continued)

FOREIGN PATENT DOCUMENTS

| | | |
|---|---|---|
| JP | 2003-175041 | 6/2003 |
| JP | 2003-250804 | 9/2003 |

(Continued)

OTHER PUBLICATIONS

U.S. Appl. No. 12/693,773, filed Jan. 26, 2010, Abe, et al.

(Continued)

*Primary Examiner* — Long V. Le
*Assistant Examiner* — Serkan Akar
(74) *Attorney, Agent, or Firm* — Oblon, Spivak, McClelland, Maier & Neustadt, L.L.P.

(57) ABSTRACT

In time phases except a first time phase, a contour tracking part tracks the position of a region of interest based on image data acquired in each of the time phases. A re-tracking part receives correction of the position of the region of interest in a second time phase, and obtains the position of the corrected region of interest in and after the second time phase based on the image data acquired in and after the second time phase. From position information of the region of interest in and before the second time phase and position information of the corrected region of interest in and after the second time phase, a position calculator obtains position information of the region of interest in all the time phases. A computing part obtains motion information of a tissue within the region of interest based on the position information of the region of interest.

14 Claims, 11 Drawing Sheets

(56) References Cited

U.S. PATENT DOCUMENTS

| | | | | |
|---|---|---|---|---|
| 6,464,642 | B1* | 10/2002 | Kawagishi | 600/454 |
| 6,638,221 | B2* | 10/2003 | Abe et al. | 600/437 |
| 7,722,540 | B2* | 5/2010 | Abe et al. | 600/443 |
| 7,766,837 | B2* | 8/2010 | Pedrizzetti et al. | 600/451 |
| 2003/0083578 | A1* | 5/2003 | Abe et al. | 600/447 |
| 2004/0111028 | A1* | 6/2004 | Abe et al. | 600/437 |
| 2005/0085729 | A1* | 4/2005 | Abe | 600/450 |
| 2005/0101863 | A1* | 5/2005 | Kawagishi et al. | 600/443 |
| 2006/0122512 | A1* | 6/2006 | Abe | 600/454 |
| 2009/0270732 | A1* | 10/2009 | Abe et al. | 600/443 |
| 2010/0074475 | A1* | 3/2010 | Chouno | 382/107 |

FOREIGN PATENT DOCUMENTS

| | | |
|---|---|---|
| JP | 2004-514526 A | 5/2004 |
| WO | WO 2008/044572 A1 | 4/2008 |

OTHER PUBLICATIONS

Office Action issued Oct. 9, 2012 in Japanese Patent Application No. 2008-114854.

* cited by examiner

ULTRASOUND IMAGING APPARATUS AND METHOD FOR PROCESSING IMAGE WITH MOTION TRACKING AND ERROR CORRECTION

BACKGROUND OF THE INVENTION

1. Field of the Invention

The present invention relates to an ultrasound imaging apparatus capable of acquiring an ultrasound image representing a subject with ultrasound waves and capable of evaluating a motional state of the subject by using the ultrasound image, and also relates to a method for processing an ultrasound image.

2. Description of the Related Art

It is very important to objectively and quantitatively evaluate the function of body tissue such as the myocardium of the heart when diagnosing the body tissue. For example, a quantitative evaluation method based on image data representing the heart that is acquired by an ultrasound imaging apparatus is proposed.

As an example, a technique of tracking using local pattern matching on a two-dimensional ultrasound image or a three-dimensional ultrasound image to calculate local wall-motion information such as displacement and strain of the myocardium (referred to as Speckle Tracking (ST) hereinafter) is practically used (e.g., Japanese Unexamined Patent Application Publication No. 2003-175041, and Japanese Unexamined Patent Application Publication No. 2003-250804).

In the ST method, the contours of the endocardium and epicardium of the myocardium are given as initial tracking positions in the end diastole (a time phase in which an initial R wave is detected) or the end systole. In the remaining time phases, the initial tracking positions are automatically tracked by using movement-vector information obtained by local pattern matching, whereby the contours of the endocardium and epicardium in all the time phases are tracked.

However, in the method according to the related art, there is a problem of occurrence of a tracking miss within one heartbeat (Problem 1).

Moreover, there is a problem of degradation of the tracking accuracy in the case of tracking over a plurality of heartbeats (Problem 2).

As for Problem 1, the contour tracking tends to deviate in a time phase T1 after a time phase T0 in which wall-motion velocity is the fastest in one heartbeat (an early diastolic phase e' in a normal case, or an atrial contraction phase a' in a diastolic dysfunction case). In this case, even if correction of the contour is made in the time phase T1 and the tracking is restarted in this time phase, the tracking will eventually deviate at the time of tracking the time phase T0 in the opposite direction.

This problem I will be described with reference to FIG. 1. FIG. 1 is a graph illustrating wall-motion velocity and strain (displacement). In FIG. 1, the horizontal axis takes a time t. A waveform pattern 500 represents the wall-motion velocity in the normal case. A waveform pattern 540 represents the wall-motion velocity in the diastolic dysfunction case. When the tracking does not deviate in the time phase e' of the normal case, the strain (displacement) is accurately evaluated as a waveform pattern 510 of the normal case. On the other hand, the wall-motion velocity in the time phase e' is the fastest within one heartbeat in the normal case. Therefore, if the tracking in the forward direction deviates, the tracking position returns to the original position in accordance with movement in the subsequent time phase a', and the strain (displacement) forms a waveform pattern 520. In this case, it is difficult to distinguish from a waveform pattern 550 in which diastolic dysfunction results from an ischemic heart disease, etc.

Thus, a case of resetting the initial tracking position in the time phase T1 and tracking in both temporal directions in this case will be considered.

However, since an error occurs in an estimated movement vector obtained by tracking in the forward direction and the tracking in the forward direction deviates, an error similarly occurs in an estimated movement vector at the time of tracking through the time phase T0 in the opposite direction.

Because the tracking in the opposite direction deviates, the peak position cannot reach the peak position at the time of tracking in the forward direction, and the peak value of the waveform decreases as shown in a waveform pattern 530. In this case, it is difficult to distinguish from a waveform pattern in which systolic failure occurs due to an ischemic heart disease or the like. In any event, it becomes difficult to accurately evaluate the normal pattern.

In order to solve this problem, when manually correcting the tracking position deviated in the time phase T1, it is necessary to manually correct the tracking position throughout the entire interval between the time phase T1 and the end of atrial systole (a time phase in which the next R wave is detected). Therefore, such correction requires time and is not easy.

As for Problem 2, in general, tracking for long time results in accumulation of errors and easy deviation of the tracking. Moreover, if movement of a subject due to breathing, etc. or movement of an ultrasound probe occurs during data acquisition, drift components are also accumulated.

As a result, the assumption of processing using periodicity (the assumption that the position returns to the original position after one heartbeat) gradually deviates, whereby the tracking accuracy is lowered.

SUMMARY OF THE INVENTION

An object of the present invention is to provide an ultrasound imaging apparatus that, in a process of tracking a region of interest, can accurately evaluate the motion of tissue included in the region of interest by correcting a tracking position with a simple operation even if the tracking position deviates, and also provide a method for processing an ultrasound image.

In a first aspect of the present invention, an ultrasound imaging apparatus comprises: an imaging part configured to scan a periodically moving subject with ultrasound waves to acquire a plurality of ultrasound image data representing the subject for one cycle or more; a region-of-interest setting part for setting a region of interest of a tissue represented in ultrasound image data acquired in a first time phase; a tracking part configured to, in time phases other than the first time phase, track a position of the region of interest for each of the time phases based on ultrasound image data acquired in each of the time phases; a re-tracking part configured to receive correction of the position of the region of interest in an arbitrary second time phase, and track the corrected position of the region of interest in and after the second time phase for each of the time phases based on ultrasound image data acquired in and after the second time phase; a position calculator configured to obtain position information of the region of interest in an interval including the first time phase and the second time phase, based on position information of the region of interest in each of the time phases in and before the second time phase and position information of the region of interest in each of the time phases in and after the second time phase obtained by the re-tracking part; a computing part configured to obtain, based on the position information of the region of interest obtained by the position calculator, motion information of the tissue included in the region of interest; and a display controller configured to cause the display to display the motion information.

According to the first aspect, in and after the second time phase, the corrected position of the region of interest is tracked for each of the time phases. Then, position information of the region of interest in an interval including the first time phase and the second time phase is obtained based on the position information of the region of interest and the position information of the region of interest in each of the time phases in and before the second time phase. Consequently, it is possible to more accurately obtain the position of the region of interest in the abovementioned interval by executing simple correction in the second time phase even if tracking by the tracking part deviates. Thus, according to the first aspect, even if the tracking position of the region of interest deviates, it is possible to correct the tracking position by a simple operation and more accurately evaluate the motion of the tissue included in the region of interest.

Further, in a second aspect of the present invention, a method for processing an ultrasound image comprises: scanning a periodically moving subject with ultrasound waves to acquire a plurality of ultrasound image data representing the subject for one cycle or more; setting a region of interest of a tissue represented in ultrasound image data acquired in a first time phase; tracking, in time phases other than the first time phase, a position of the region of interest for each of the time phases based on ultrasound image data acquired in each of the time phases; receiving correction of the position of the region of interest in an arbitrary second time phase, and re-tracking the corrected position of the region of interest in and after the second time phase for each of the time phases based on ultrasound image data acquired in and after the second time phase; obtaining, based on position information of the region of interest in each of the time phases in and before the second time phase and position information of the region of interest in each of the time phases in and after the second time phase obtained by the re-tracking, position information of the region of interest in an interval including the first time phase and the second time phase; obtaining, based on the position information of the region of interest in the interval including the first time phase and the second time phase, motion information of the tissue included in the region of interest; and displaying the motion information.

DETAILED DESCRIPTION OF THE EMBODIMENTS

First Embodiment

Figure 1:
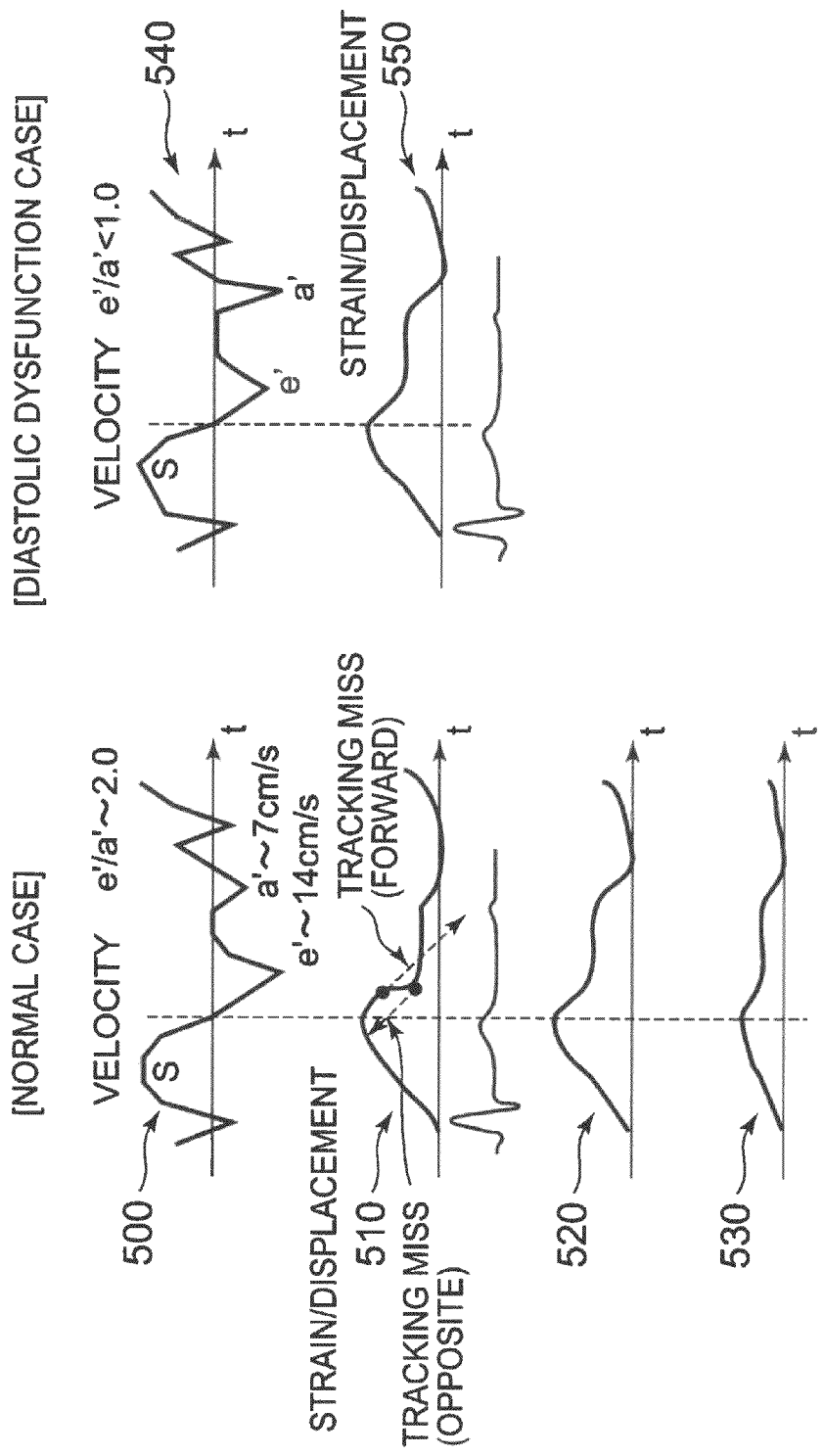
FIG. 1 is a graph illustrating wall-motion information and strain (displacement).
Figure 2:
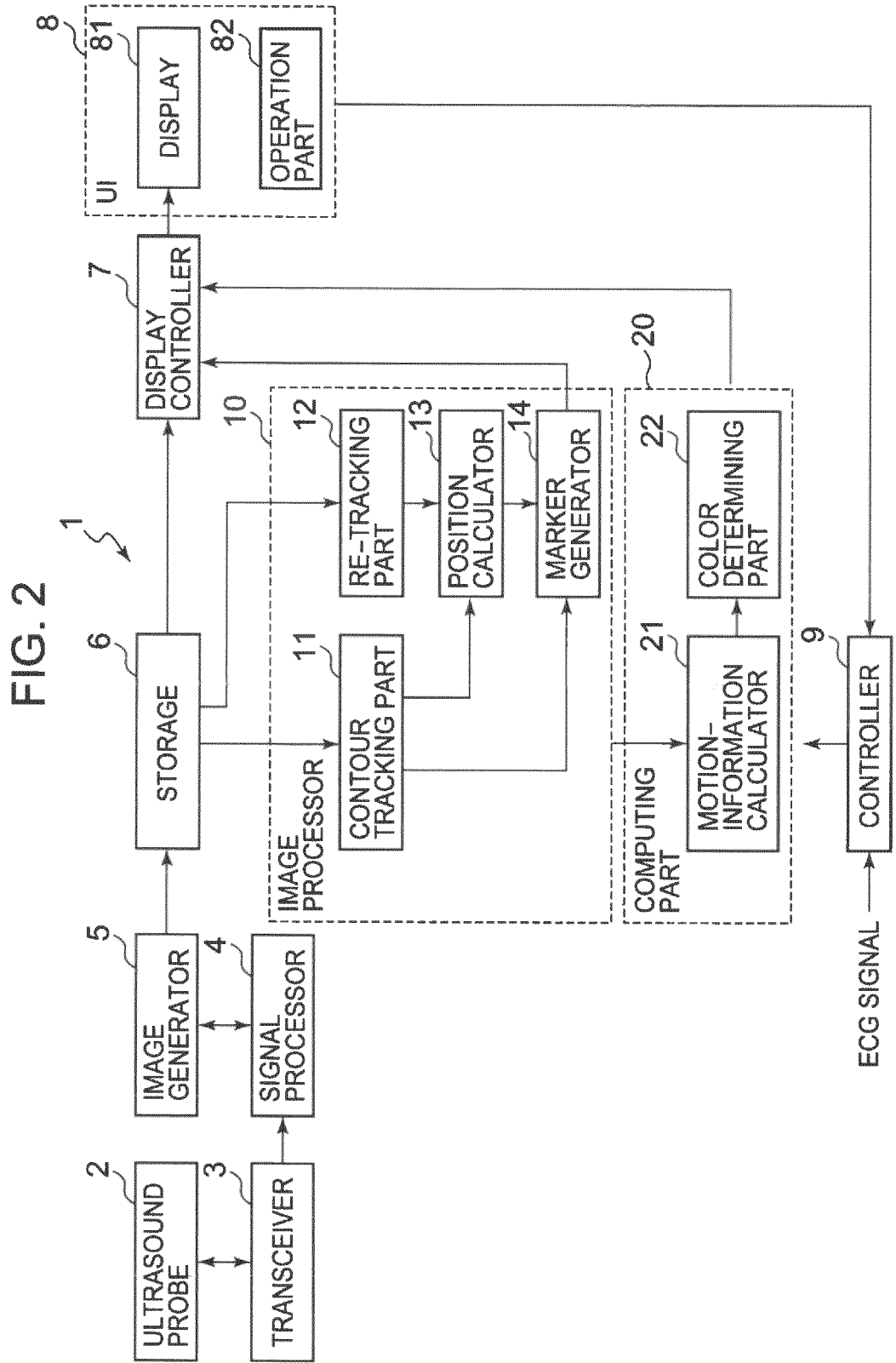
FIG. 2 is a block diagram illustrating an ultrasound imaging apparatus according to an embodiment of the present invention.

An ultrasound imaging apparatus according to a first embodiment of the present invention will be described with reference to FIG. 2. FIG. 2 is a block diagram illustrating the ultrasound imaging apparatus according to the first embodiment of the present invention.

An ultrasound imaging apparatus 1 according to the first embodiment includes an ultrasound probe 2, a transceiver 3, a signal processor 4, an image generator 5, a storage 6, a display controller 7, a user interface (UI) 8, a controller 9, an image processor 10, and a computing part 20. Moreover, an ultrasound image processing apparatus may be composed of the storage 6, the display controller 7, the user interface (UI) 8, the image processor 10, and the computing part 20.

As the ultrasound probe 2, a 1D array probe having a plurality of ultrasound transducers aligned in a predetermined direction (a scanning direction) or a 2D array probe having a plurality of ultrasound transducers two-dimensionally arranged is used. Alternatively, a 1D array probe in which ultrasound transducers are aligned in a predetermined direction (a scanning direction) and can be mechanically oscillated in a direction (an oscillating direction) orthogonal to the scanning direction may be used.

The transceiver 3 includes a transmitter and a receiver. The transceiver 3 supplies electrical signals to the ultrasound probe 2 so as to generate ultrasound waves, and receives echo signals received by the ultrasound probe 2.

The transmitter of the transceiver 3 includes a clock generation circuit, a transmission delay circuit, and a pulsar circuit, which are not shown in the drawings. The clock generation circuit generates clock signals that determine the transmission timing and transmission frequency of the ultrasound signals.

The transmission delay circuit executes transmission focus by applying a delay at the time of transmission of ultrasound waves. The pulsar circuit has the same number of pulsars as individual channels corresponding to the respective ultrasound transducers, generates a driving pulse at the delayed transmission timing, and supplies electrical signals to the respective ultrasound transducers of the ultrasonic probe 2.

The receiver of the transceiver 3 includes a preamplifier circuit, an A/D conversion circuit, a reception delay circuit, and an adder circuit. The preamplifier circuit amplifies echo signals outputted from the respective ultrasound transducers of the ultrasound probe 2, for each of the reception channels. The A/D conversion circuit executes A/D conversion on the amplified echo signals. The reception delay circuit applies a delay time necessary for determining the reception directionality of the echo signals after the A/D conversion. The adder circuit adds the delayed echo signals.

With such an addition, a reflection component from a direction according to reception directionality is enhanced. Here, the signals after the addition process by the transceiver 3 may be referred to as "RF data (raw data)." The transceiver 3 outputs the RF data to the signal processor 4.

The ultrasound probe 2 and the transceiver 3 compose an example of an "imaging part" of the present invention.

The signal processor 4 includes a B-mode processor, a CFM processor, etc. The B-mode processor visualizes amplitude information of the echoes.

More specifically, the B-mode processor executes a band pass filter process on the reception signals outputted from the transceiver 3, and thereafter detects the envelope curve of the output signals. The B-mode processor then executes a compression process by logarithmic transformation on the detected data, thereby visualizing the amplitude information of the echoes. Moreover, the CFM processor visualizes moving blood-flow information. Blood-flow information includes information such as velocity, dispersion and power, and is obtained as binary information.

The image generator 5 converts the data after the signal processing into coordinate system data based on a space coordinate (digital scan conversion). For example, the image generator 5 executes scan conversion on the data after the signal processing outputted from the B-mode processor, thereby generating B-mode image data representing the shape of tissues of a subject (referred to as "image data" hereinafter). The image generator 5 then outputs ultrasound image data such as the image data to the storage 6.

Further, when volume scan is being performed by the ultrasound probe 2 and the transceiver 3, the image generator 5 may receive volume data from the signal processor 4 and executes volume rendering on the volume data, thereby generating three-dimensional image data representing the tissue in three dimensions. Furthermore, the image generator 5 may execute the MPR (Multi Planar Reconstruction) process on the volume data, thereby generating image data (MPR image data) on an arbitrary cross section. The image generator 5 then outputs ultrasound image data such as the three-dimensional image data and the MPR image data to the display controller 6.

The ultrasound image data such as the image data and the three-dimensional image data generated by the image generator 5 is stored into the storage 6. Moreover, in a case that ECG (electrocardiogram) signals of the subject have been acquired, the controller 9 receives the ECG signals from outside the ultrasound imaging apparatus 1, and causes the storage 6 to store the ultrasound image data associated with a cardiac phase received in a timing of generation of the ultrasound image data.

The ultrasound imaging apparatus 1 according to the first embodiment scans the heart of a subject with ultrasound waves, thereby acquiring image data representing the heart in each cardiac phase. For example, the ultrasound imaging apparatus 1 scans the heart of a subject with ultrasound waves for one cardiac cycle or more, thereby acquiring a plurality of image data (moving image data representing the heart) for one cardiac cycle or more.

Moreover, in a case that ECG signals are acquired already, the controller 9 causes the storage 6 to store each of the image data associated with a cardiac phase received in a timing that the image data has been generated. Consequently, each of the plurality of image data is associated with a cardiac phase that the image data has been generated, and stored into the storage 6.

The display controller 7 reads image data from the storage 6 and causes a display 81 to display an image based on the image data. For example, when an operator designates an arbitrary cardiac phase by using an operation part 82, information representing the designated cardiac phase is outputted from the user interface (UI) 8 to the display controller 7. The display controller 7 reads image data associated with the designated cardiac phase from the storage 6 and causes the display 81 to display an image based on the image data.

(Image Processor 10)

The image processor 10 includes a contour tracking part 11, a re-tracking part 12, a position calculator 13, and a marker generator 14. The image processor 10 sets the contour (a region of interest) of specific tissue designated on an image representing the heart as an initial contour, and executes pattern matching on two images acquired in different cardiac phases, thereby obtaining the position of the contour in each of the cardiac phases.

Now, a method for designating the abovementioned initial contour (region of interest) will be described. In this embodiment, assuming the specific tissue is the heart, designation of the contours of the endocardium and epicardium of the heart will be described. First, the operator designates an arbitrary cardiac phase by using the operation part 82. The display controller 7 reads image data acquired in the cardiac phase designated by the operator, and causes the display 81 to display an image based on the image data. In this embodiment, because image data representing the heart is acquired, an image representing the heart is displayed on the display 81. For example, scan of a cross section along the long-axis direction of the heart (may be referred to as a "long-axis cross section" hereinafter) is executed by the ultrasound probe 2 and the transceiver 3, whereby image data on the long-axis cross section (may be referred to as "long-axis view data" hereinafter) is acquired. The display controller 7 then causes the display 81 to display a long-axis view based on the long-axis view data acquired in the cardiac phase designated by the operator.

For example, when the end diastole or the end systole is designated by the operator, the display controller 7 reads image data acquired in the end diastole or image data acquired in the end systole from the storage 6, and causes the display 81 to display an image based on the image data. Since the image data is stored in the storage 6 in association with a cardiac phase in which the image data has been acquired, the display controller 7 reads image data from the storage 6 acquired in a cardiac phase such as the end diastole and the end systole, and causes the display 81 to display an image based on the image data in the cardiac phase.

Then, the operator traces the two-dimensional contour of the endocardium shown on the image by using the operation part 82, thereby designating the two-dimensional contour of the endocardium on the image.

When the two-dimensional contour of the endocardium is thus designated, coordinate information representing the position of the two-dimensional contour of the endocardium is outputted from the user interface (UI) 8 to the image processor 10 via the controller 9.

Furthermore, the operator traces the two-dimensional contour of the epicardium shown on the image by using the operation part 82, thereby designating the two-dimensional contour of the epicardium on the image.

When the two-dimensional contour of the epicardium is thus designated, coordinate information representing the position of the two-dimensional contour of the epicardium is outputted from the user interface (UI) 8 to the image processor 10 via the controller 9.

(Contour Tracking Part 11)

In the image processor 10, the contour tracking part 11 receives the coordinate information of the contour of the endocardium and the coordinate information of the contour of the epicardium from the user interface (UI) 8.

The two-dimensional contours of the endocardium and the epicardium designated here are set as the initial contours of the endocardium and the epicardium in the contour tracking part 11. For example, two-dimensional contours of the endocardium and the epicardium in a cardiac phase in which an R wave has been detected is set as the initial contours.

As described above, when the operator designates the two-dimensional contour of the endocardium in an arbitrary cardiac phase (the initial contour of the endocardium), the contour tracking part 11 executes pattern matching using a speckle pattern on the two image data acquired at different times (ST process). In this pattern matching, the contour tracking part 11 obtains the position of each of the points composing the two-dimensional contour of the endocardium, for each image data acquired in each cardiac phase. The contour tracking part 11 then obtains the position of each of the points on the two-dimensional contour of the endocardium, for each image data generated in each cardiac phase. As described above, the contour tracking part 11 temporally tracks each of the points composing the two-dimensional contour of the endocardium.

For example, the contour tracking part 11 receives coordinate information of each of the points composing the contour of the endocardium set as the initial contour, and moreover reads, from the storage 6, image data (may be referred to as "image data B" hereinafter) generated in a cardiac phase next to the image data (may be referred to as "image data A" hereinafter) in which the initial contour has been set. The contour tracking part 11 then obtains the movement vector of each of the points composing the contour of the endocardium by executing pattern matching using a speckle pattern on the two images that are temporally continuous. More specifically, the contour tracking part 11 obtains the movement vector of each of the points composing the contour of the endocardium by executing pattern matching using a speckle pattern on the image A and the image B. This movement vector represents displacement of each of the points composing the contour and a movement direction in which each of the points has displaced.

In other words, the contour tracking part 11 executes pattern matching on the two images and calculates the movement amount of a speckle pattern, thereby obtaining the movement vector of each of the points composing the contour. By thus obtaining the movement vector of each of the points composing the contour, the position of each of the points composing the contour of the endocardium in the cardiac phase in which the image data B has been generated is obtained.

Furthermore, the contour tracking part 11 reads, from the storage 6, image data (may be referred to as "image data C" hereinafter) generated in a cardiac phase next to the image data B. Then, the contour tracking part 11 executes pattern matching using a speckle pattern on the two temporally continuous image data (image data B and image data C), thereby obtaining the movement vectors of the respective points composing the contour of the endocardium. Consequently, the positions of the respective points composing the contour of the endocardium in the cardiac phase of generation in which the image data C has been generated are obtained.

As described above, by executing pattern matching using a speckle pattern (ST process), the contour tracking part 11 obtains the movement vectors of the respective points composing the contour of the endocardium, for each cardiac phase in which each image data has been generated. Thus, the contour tracking part 11 temporally tracks the movement vectors of the respective points composing the contour of the endocardium. As a result, it becomes possible to temporally track the respective points composing the two-dimensional contour of the endocardium. For example, the contour tracking part 11 obtains the positions of the respective points composing the two-dimensional contour of the endocardium in each cardiac phase, for the total image data acquired within one cardiac cycle. Consequently, the positions of the respective points composing the two-dimensional contour of the endocardium in each cardiac phase are obtained for one cardiac cycle.

Further, when the two-dimensional contour of the epicardium (the initial contour of the epicardium) is set, the contour tracking part 11 executes pattern matching using a speckle pattern on two image data acquired at different times, as in the tracking of the endocardium. By executing this pattern matching, the contour tracking part 11 obtains the positions of the respective points composing the two-dimensional contour of the epicardium, for each image data generated in each cardiac phase. Thus, the contour tracking part 11 temporally tracks the respective points composing the two-dimensional contour of the epicardium.

The contour tracking part 11 may obtain a normal vector at each of the points composing a designated endocardium and define a position that is a certain distance outside each of the points on the endocardium in the normal vector direction, as the two-dimensional contour of the epicardium of the heart. For example, the contour tracking part 11 defines a position that is 8 mm outside the position of the endocardium as the contour of the epicardium.

This certain distance may be changed to an arbitrary value by the operator. The two-dimensional contour of the epicardium defined here is set in the contour tracking part 11 as the initial contour of the epicardium to be tracked. The contour tracking part 11 then temporally tracks the respective points composing the two-dimensional contour of the epicardium.

The contour tracking part 11 outputs coordinate information of the respective points composing the two-dimensional contour of the endocardium and coordinate information of the respective points composing the two-dimensional contour of the epicardium in the respective cardiac phases, to the position calculator 13, the marker generator 14, and the computing part 20.

The contour tracking part 11 is equivalent to an example of the "tracking part" in the present invention.

(Computing Part 20)

The computing part 20 includes a motion-information calculator 21 and a color determining part 22.

(Motion-Information Calculator 21)

The motion-information calculator 21 receives the coordinate information of the respective points composing the two-dimensional contour of the endocardium in each cardiac phase and the coordinate information of the respective points composing the two-dimensional contour of the epicardium in each cardiac phase, from the image processor 10, and obtains wall-motion information of the myocardium. As an example, the motion-information calculator 21 obtains a wall-thickness change rate (Transversal Strain [%]) in the wall-thickness direction in each cardiac phase, based on the coordinate information of the respective points composing the two-dimensional contour of the endocardium and the coordinate information of the respective points composing the two-dimensional contour of the epicardium in each cardiac phase. Here, the wall-thickness change rate is defined as a strain in the thickness direction between the endocardium and the epicardium. Moreover, the motion-information calculator 21 may obtain a strain rate (Transversal Strain Rate [1/s]) representing temporal differentiation of the wall-thickness change rate.

For example, the motion-information calculator 21 obtains a line orthogonal to the contour of the endocardium, at a point on the contour of the endocardium. The motion-information calculator 21 then obtains a point on the contour of the epicardium intersecting the orthogonal line. The motion-information calculator 21 obtains the wall-thickness change rate between the endocardium and the epicardium in each cardiac phase, based on the distance between the point on the contour of the endocardium and the point on the contour of the epicardium in each cardiac phase. Further, the motion-information calculator 21 obtains the wall-thickness change rate between the contour of the endocardium and the contour of the epicardium at predetermined intervals. In other words, the motion-information calculator 21 obtains the wall-thickness change rates between the endocardium and the epicardium of the heart at a plurality of sites. Thus, the motion-information calculator 21 obtains the wall-thickness change rates at the respective sites of the myocardium for each cardiac phase. Moreover, the motion-information calculator 21 may temporally differentiates the wall-thickness change rates at the respective sites in each cardiac phase, thereby obtaining a strain rate for each cardiac phase.

(Color Determining Part 22)

The color determining part 22 determines colors corresponding to the magnitudes of the wall-motion information at the respective sites obtained by the motion-information calculator 21, and assigns different colors in accordance with the magnitudes to the respective sites. For example, colors assigned to the magnitudes of the wall-thickness change rates are determined beforehand. A look up table (LUT) in which the magnitudes of the wall-thickness change rates are associated with colors is previously created and stored in a storage, which is not shown. In this table, colors are associated so as to be different depending on the magnitudes of the wall-thickness change rates. With reference to the table, the color determining part 22 determines a color associated with the magnitude of the wall-thickness change rate at each of the sites in each cardiac phase. Then, the color determining part 22 outputs the coordinate information of each of the sites in each cardiac phase and information representing the color assigned to the site (color information) to the display controller 7.

(Marker Generator 14)

The marker generator 14 of the image processor 10 generates an endocardium marker representing the shape of the contour of the endocardium based on the coordinate information of the two-dimensional contour of the endocardium designated by the operator. Similarly, the marker generator 14 generates an epicardium marker representing the shape of the contour of the epicardium based on the coordinate information of the two-dimensional contour of the epicardium designated by the operator. The marker generator 14 then outputs coordinate information representing the position of the endocardium marker and coordinate information representing the position of the epicardium marker to the display controller 7. The display controller 7 causes the display 81 to display an image based on the image data in which the initial contour has been designated, and moreover, specifies a display position of each of the markers on the image based on the coordinate information of each of the markers and causes the display 81 to display the endocardium marker and the epicardium marker so as to be superimposed on the image.

Further, when receiving the coordinate information of the respective points composing the two-dimensional contour of the endocardium in each cardiac phase from the contour tracking part 11, the marker generator 14 generates the endocardium marker representing the shape of the contour of the endocardium in each cardiac phase. Similarly, when receiving the coordinate information of the respective points composing the two-dimensional contour of the epicardium in each cardiac phase from the contour tracking part 11, the marker generator 14 generates the epicardium marker representing the shape of the contour of the epicardium in each cardiac phase.

The marker generator 14 outputs the coordinate information of the endocardium marker and the coordinate information of the epicardium marker in each cardiac phase to the display controller 7. The display controller 7 causes the display 81 to sequentially display an image based on the image data acquired in each cardiac phase, for each cardiac phase. Furthermore, the display controller 7 specifies a display position of the endocardium marker on the image based on the coordinate information of the endocardium marker in each cardiac phase, and causes the display 81 to sequentially display the endocardium marker in each cardiac phase so as to be superimposed on the image in each cardiac phase. Similarly, the display controller 7 specifies a display position of the epicardium marker on the image based on the coordinate information of the epicardium marker in each cardiac phase, and causes the display 81 to sequentially display the epicardium marker in each cardiac phase so as to be superimposed on the image in each cardiac phase.

Then, the display controller 7 sequentially updates the images and the markers, and causes the display 81 to display them.

Furthermore, the display controller 7 receives, from the color determining part 22, the coordinate information of each site of the myocardium in each cardiac phase and the information representing the color assigned to each site. Then, the display controller 7 assigns the color determined by the color determining part 22 to each site of the myocardium on the image in each cardiac phase, and causes the display 81 to display. For example, the display controller 7 assigns the color determined by the color determining part 22 to each site of a region between the endocardium marker and the epicardium marker, and causes the display 81 to display. The display controller 7 assigns the color determined for each site to a range having a predetermined width around each site, and causes the display 81 to display.

Then, the display controller 7 sequentially updates the image acquired in each cardiac phase, the endocardium marker representing the contour of the endocardium, the epicardium marker representing the contour of the epicardium and the wall-motion information for each cardiac phase, and causes the display 81 to display them.

(Re-Tracking Part 12)

The re-tracking part 12 receives coordinate information representing the position of a contour corrected in an arbitrary cardiac phase and, assuming the corrected contour as the initial contour, executes pattern matching using a speckle pattern (ST process) on images acquired in and after the arbitrary cardiac phase, thereby obtaining the contour position in each cardiac time phase in and after the arbitrary cardiac time phase.

First, when the operator gives an instruction for correction by using the operation part 82, the instruction is outputted to the controller 9. The controller 9 gives the instruction for correction to the image processor 10.

Then, the operator designates, by using the operation part 82, an arbitrary cardiac phase in which the contour position of the endocardium or the epicardium is corrected. The display controller 7 causes the display 81 to display an image based on the image data acquired in the designated cardiac phase.

For example, in the case of correcting the contour position of the endocardium, the operator designates a new two-dimensional contour of the endocardium by using the operation part 82 with reference to the endocardium represented on the image. As an example, the operator compares the contour position of the endocardium represented on the image with the contour position obtained in the ST process by the contour tracking part 11, and determines whether the tracking position deviates or conforms. Since the contour position of the endocardium obtained in the ST process by the contour tracking part 11 is represented on the image by the endocardium marker, the necessity of correction can be determined by comparing the position of the endocardium marker with the contour position of the endocardium represented on the image. As for the epicardium, the necessity of correction is also determined by comparing the position of the epicardium marker with the contour position of the epicardium represented on the image.

Then, the operator corrects, based on the contour of the endocardium represented on the image, the contour position of the endocardium obtained in the ST process by the contour tracking part 11 to the expected position by using the operation part 82. For example, the operator designates a new contour position of the endocardium by using the operation part 82. When the new contour position of the endocardium is thus designated, coordinate information representing the new contour position is outputted from the user interface (UI) 8 to the image processor 10 via the controller 9. The re-tracking part 12 then sets the new contour of the endocardium as the initial contour and executes the ST process on the images acquired in and after the cardiac phase designated by the operator, thereby obtaining the positions of the contour of the endocardium in and after the cardiac phase. Also in the case of correcting the contour position of the epicardium, the operator designates a new contour position of the epicardium by using the operation part 82. The re-tracking part 12 then sets the new contour of the epicardium as the initial contour, and obtains positions of the epicardium in and after the cardiac phase designated by the operator. The re-tracking part 12 then outputs the coordinate information of the contour in each cardiac phase in and after the cardiac phase designated by the operator to the position calculator 13. The re-tracking part 12 is equivalent to an example of the "re-tracking part" in the present invention.

On the other hand, when an instruction for re-tracking is given by the operator, the coordinate information of the contour in each cardiac phase in and before the cardiac phase designated by the operator is outputted from the contour tracking part 11 to the position calculator 13, and the coordinate information is retained in the position calculator 13. To be specific, the contour tracking part 11 outputs, to the position calculator 13, the coordinate information representing the contour position of the endocardium and the coordinate information representing the contour position of the epicardium in each cardiac phase in and before the cardiac phase designated by the operator.

The position calculator 13 retains the contour position of the endocardium and the contour position of the epicardium in each cardiac phase.

(Position Calculator 13)

The position calculator 13 retains the coordinate information of the contour in each cardiac phase in and before the cardiac phase designated by the operator. Furthermore, the position calculator 13 receives the coordinate information of the contour re-tracked by the re-tracking part 12 from the re-tracking part 12 and obtains, based on the coordinate information of the contour in and before the cardiac phase in which the correction has been designated by the operator, and the coordinate information of the re-tracked contour, positions of the contour at all time phases. At this moment, it is preferable for the position calculator 13 to smooth, at the cardiac phase to which the correction has been designated, the contour position in the time direction, thereby smoothly linking the contour in the vicinity of the designated cardiac phase. The position calculator 13 is equivalent to an example of the "position calculator" in the present invention.

As an example, a case in which the ST process is executed within one heartbeat (from the time phase T0 to the time phase Tend) to execute tracking of the contour position and the tracking of the contour position deviates in the time phase e' (time phase T1) of diastole will be described.

(Step S01)

First, the operator designates a desired heartbeat (from the time phase T0 to the time phase Tend) by using the operation part 82. When a desired heartbeat is designated, information representing time phase T0 to the time phase Tend is outputted from the user interface (UI) 8 to the image processor 10 and the display controller 7.

(Step S02)

The operator designates the position of the initial contour in the initial time phase by using the operation part 82. More specifically, the display controller 7 reads the image data in the initial time phase from the storage 6 and causes the display 81 to display an image based on the image data. For example, when the operator designates the time phase T0 as the initial time phase by using the operation part 82, the display controller 7 causes the display 81 to display an image in the time phase T0. The operator then designates the position of the initial contour of the endocardium and the position of the initial contour of the epicardium on the image by using the operation part 82 as described above.

(Step S03)

The contour tracking part 11 sets the initial contours designated by the operator as targets for tracking and performs ST process on image data acquired within one heartbeat (between the time phase T0 and the time phase Tend), thereby obtaining the contour position of the endocardium and the contour position of the epicardium in each cardiac phase between the time phase T0 and the time phase Tend.

The display controller 7 then causes the display 81 to display, in the order of the cardiac phases, the endocardium marker and the epicardium marker so as to be superimposed on the image in each cardiac phase. The operator compares the contour of the endocardium represented on the image in each cardiac phase with the position of the endocardium marker to determine the necessity of correcting the contour position. As for the epicardium, the operator also compared to the contour of the epicardium represented on the image in each cardiac phase with the position of the epicardium marker in order to determine the necessity of correcting the contour position.

(Step S04)

For example, in a case that the contour position of the endocardium obtained by the ST process deviates from the tracking in the time phase e' of diastole (time phase T1), the contour position of the endocardium obtained by the ST process is corrected in the time phase T1. When the operator designates the time phase T1 by using the operation part 82, the display controller 7 causes the display 81 to display an image in the time phase T1.

The operator compares the endocardium represented on the image in the time phase T1 with the contour of the endocardium (the endocardium marker) obtained by the ST process, and corrects the contour position of the endocardium obtained by the ST process. In other words, the operator designates a new contour position of the endocardium by using the operation part 82. When the new contour position of the endocardium is thus designated by the operator, coordinate information representing the new contour position is outputted from the user interface (UI) 8 to the re-tracking part 12 via the controller 9. Then, the new contour position is set in the re-tracking part 12 as the initial contour of the endocardium.

(Step S05)

The re-tracking part 12 executes the ST process on each of the image data acquired during the interval between the time phase T1 and the last time phase Tend with the newly designated endocardium contour as the initial contour, thereby obtaining a contour position P1 of the endocardium in each cardiac phase during the interval between the time phase T1 and the time phase Tend. Consequently, the contour position of the endocardium is updated during the interval between the time phase T1 and the time phase Tend. Then, the re-tracking part 12 outputs the coordinate information of the contour position P1 of the endocardium in each cardiac phase during the interval between the time phase T1 and the time phase Tend, to the position calculator 13.

On the other hand, when an instruction for re-tracking is given by the operator, the coordinate information of the contour in each cardiac phase in and before the cardiac phase designated by the operator is outputted from the contour tracking part 11 to the position calculator 13, and the coordinate information is retained in the position calculator 13. In the first embodiment, the coordinate information representing the contour position P0 of the endocardium in each cardiac phase during the position between the time phase T0 and the time phase T1 is retained in the position calculator 13.

(Step S06)

Then, in the time phase T1, the position calculator 13 connects the contour position P0 of the endocardium in each cardiac phase during the interval between the time phase T0 and the time phase T1 with the contour position P1 of the endocardium in each cardiac phase during the interval between the time phase T1 and the time phase Tend, thereby obtaining the contour position of the endocardium for one heartbeat. Furthermore, in the time phase T1, the position calculator 13 smoothes the contour position P0 and the contour position P1 in the time direction, thereby smoothly coupling the contour position P0 with the contour position P1.

The position calculator 13 then outputs coordinate information of the contours in all of the time phases during the interval between the time phase T0 and the time phase Tend, to the marker generator 14 and the computing part 20. As described above, the marker generator 14 generates, based on the coordinate information of the contour in each cardiac phase, a marker of the contour in each cardiac phase. Moreover, the motion-information calculator 21 of the computing part 20 obtains, based on the coordinate information of the contour in each cardiac phase, wall-motion information in each cardiac phase. The display controller 7 then sequentially updates the images, the markers, and the wall-motion information and causes the display 81 to display them.

With the above process, the operator can automatically and easily obtain a more accurate tracking position in the total interval between the time phase T1 and the time phase Tend, simply by executing a correcting operation in only one time phase (time phase T1) in which the tracking has deviated, and then executing a re-tracking process. Consequently, it is possible to obtain more accurate wall-motion information in a simple operation, even when the tracking of the contour position deviates.

This embodiment is characterized by the process in Step S05. That is to say, since the tracking position is hard to deviate in an interval from the time phase T0 up to right before the time phase T1, which is before the diastole showing the fastest velocity, it is believed that the tracking position is accurate until immediately before the time phase T1. Moreover, even if the tracking deviates in the time phase T1, the position in the time phase T1 is also accurate after the operator visually corrects the position at the deviation position. Since the contour position P0 in the interval between the time phase T0 and the time phase T1 is accurate at this moment, the contour position P0 is retained in the position calculator 13 as shown in Step S05. On the other hand, though all of the contour positions in the interval between the time phase T1 and the time phase Tend should be corrected, it is possible, by executing the ST process until the time phase Tend with the corrected contour position in the time phase T1 as the initial contour, to automatically obtain more accurate tracking positions in the interval between the time phase T1 and the time phase Tend.

Further, as shown in Step S06, it is preferable to execute a smoothing process by the position calculator 13. In the ST process, for the inertia of a living body, it is general to execute a smoothing process in the time direction to exclude change of a position that is temporally too precipitous. Therefore, change of the contour position is relatively smooth due to the ST process in the interval from the time phase T0 up to immediately before the time phase T1. Also in the interval from the time phase T1 to the time phase Tend, change of the contour position is relatively smooth due to the ST process.

However, in the interval immediately between right before the time phase T1 and the time phase T1, a gap between the contour positions due to the correction is made. Thus, in order to reduce this gap, it is preferable to execute the smoothing process in the time direction, in the vicinity of the time phase T1 in which the contour position P0 and the contour position P1 are connected. Consequently, it is possible to suppress a gap of the contours and smoothly connect the contours in the vicinity of the time phase T1.

A specific example of the first embodiment will be described with reference to FIGS. 3 through 6. FIGS. 3 through 6 are views illustrating an image and wall-motion information acquired by the ultrasound imaging apparatus according to the first embodiment.

Figure 3:
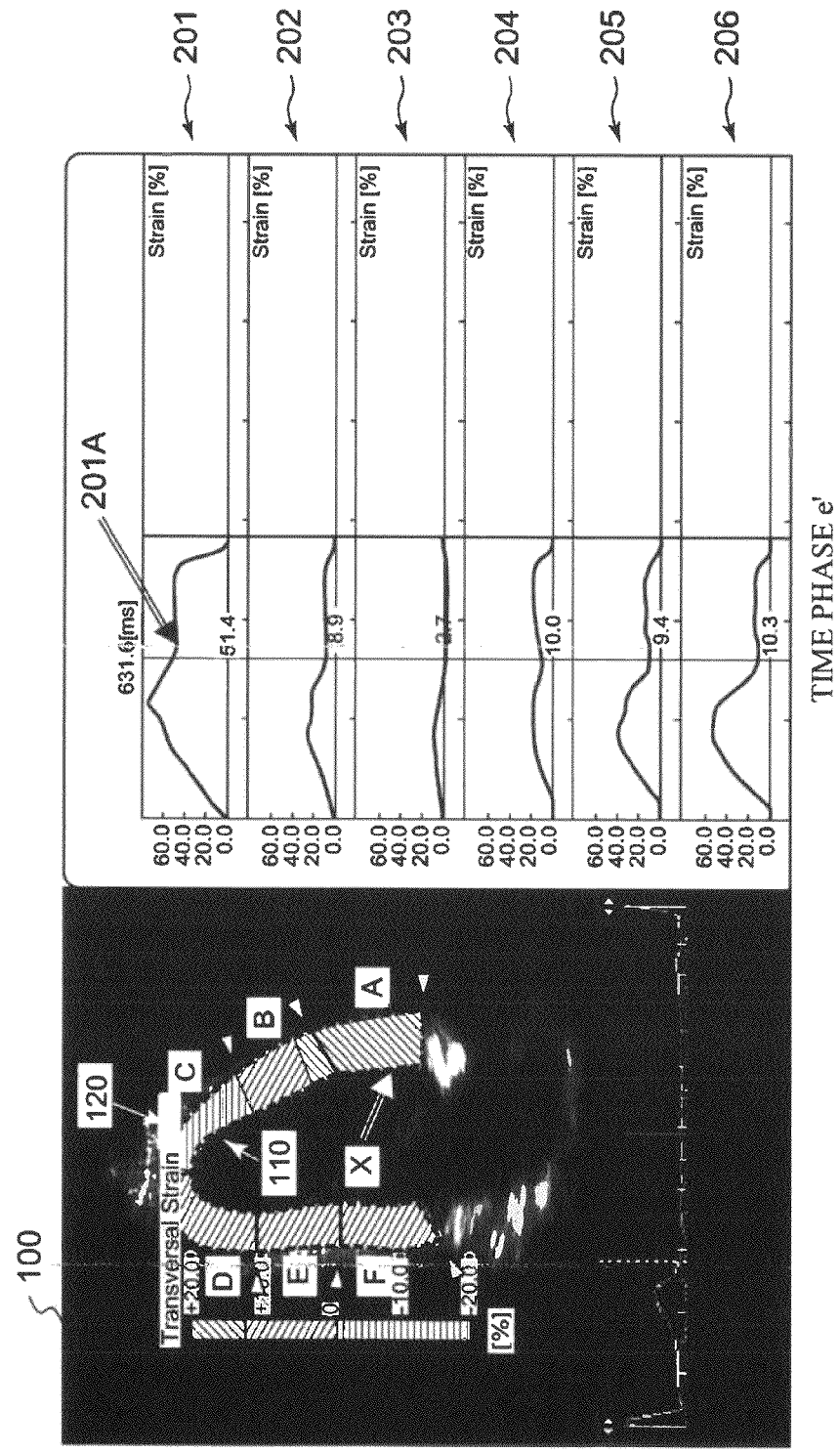
FIG. 3 is a view illustrating an image and wall-motion information acquired by an ultrasound imaging apparatus according to a first embodiment.

First, the processes from Step S01 to Step S03 described above are executed. FIG. 3 shows the result of the processes up to Step S03. As an example, the display controller 7 causes the display 81 to display a long-axis view 100, and additionally causes the display 81 to display an endocardium marker 110 and an epicardium marker 120 so as to be superimposed on the long-axis view 100. The long-axis view 100 shown in FIG. 3 is an image acquired in the time phase e'. Furthermore, the display controller 7 causes the display 81 to display wall-motion information obtained by the motion-information calculator 21. As an example, the display controller 7 causes the display 81 to display a graph 201 representing the temporal change of the wall-thickness change rate (Transversal Strain) in a region A of the myocardium. Similarly, the display controller 7 causes the display 81 to display a graph 202 representing the wall-thickness change rate in a region B of the myocardium, a graph 203 representing the wall-thickness change rate in a region C, a graph 204 representing the wall-thickness change rate in a region D, a graph 205 representing the wall-thickness change rate in a region E, and a graph 206 representing the wall-thickness change rate in a region F.

In the graphs 201 through 206, the horizontal axis takes the time phase and the vertical axis takes the wall-thickness change rate (Transversal Strain) [%]. In the example shown in FIG. 3, as indicated by an arrow X and an arrow 201A, tracking of the contour position deviates in the basal anterior wall in and after the time phase e'. Moreover, when receiving coordinate information of each site of the myocardium in each cardiac phase and information representing the color assigned to each site from the color determining part 22, the display controller 7 assigns the color determined for each site to each site of the range between the endocardium and the epicardium represented on the long-axis view 100, and causes the display 81 to display it. For example, the display controller 7 assigns a color associated with the magnitude of the wall-thickness change rate to each site between the endocardium marker 10 and the epicardium marker 120, and causes the display 81 to display it so as to be superimposed on the long-axis view 100.

Figure 4:
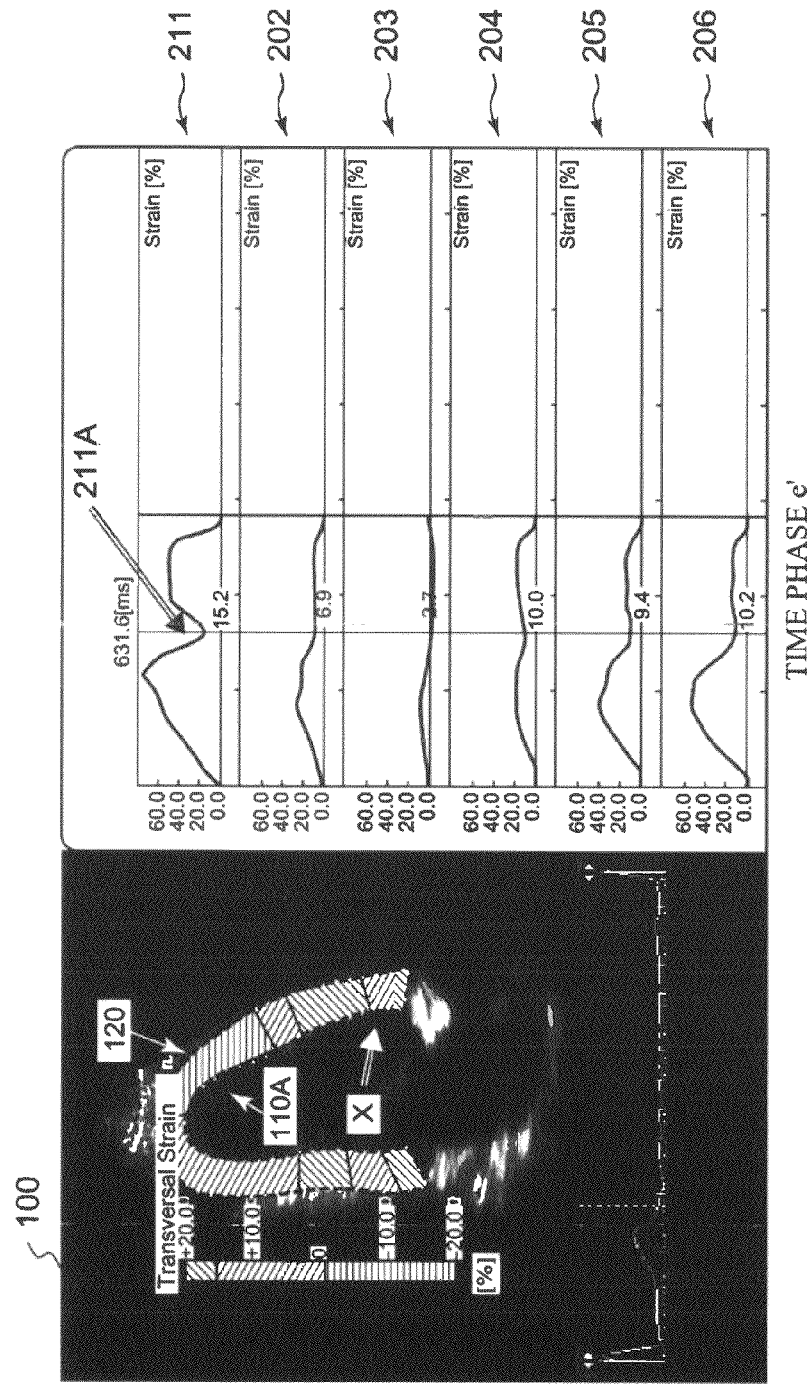
FIG. 4 is a view illustrating an image and wall-motion information acquired by the ultrasound imaging apparatus according to the first embodiment.

Then, with reference to the long-axis view 100 in the time phase e', the operator corrects the contour positions obtained in the ST process by using the operation part 82. For example, the operator compares the contour position of the endocardium shown on the long-axis view 100 with the position of the endocardium marker 110, and correct the contour position obtained in the ST process. Also regarding the epicardium, the operator compares the contour position of the epicardium shown on the long-axis view 100 with the position of the epicardium marker 120, and corrects the contour position obtained in the ST process. For example, as shown in FIG. 4, the operator corrects the contour position of the endocardium in the basal anterior wall shown with the arrow X by using the operation part 82. The coordinate information representing the corrected contour position of the endocardium is outputted from the user interface (UI) 8 to the image processor 10 and the computing part 20.

The marker generator 14 generates an endocardium marker representing the shape of the contour of the endocardium, based on the coordinate information of the two-dimensional contour of the endocardium designated by the operator. Then, as shown in FIG. 4, the display controller 7 causes the display 81 to display an endocardium marker 110A representing the corrected contour of the endocardium so as to be superimposed on the long-axis view 100.

Further, the motion-information calculator 21 newly obtains wall-motion information based on the coordinate information of the two-dimensional contour of the endocardium designated by the operator. As an example, the display controller 7 causes the display 81 to display a new graph 211 representing the wall-thickness change rate (Transversal Strain). In accordance with the correction of the contour, the value of the wall-thickness change rate varies in the vicinity of the time phase e' (a portion indicated with an arrow 211A). Thus, in accordance with the correction of the contour, the value of the graph is also corrected.

Then, the re-tracking part 12 sets the contour designated in the time phase e' as the initial contour, and executes the ST process on the images acquired in and after the time phase e', thereby newly obtaining the contour position in each cardiac phase in and after the time phase e'. Then, the position calculator 13 connects the contour position in each cardiac phase in and before the time phase e' with the contour position in each cardiac phase in and after the time phase e', thereby obtaining the contour positions in the total interval. Moreover, the marker generator 14 generates an endocardium marker and an epicardium marker in each cardiac phase, based on the coordinate information of the contour in each cardiac phase. The motion-information calculator 21 of the computing part 20 obtains motion information in each cardiac phase, based on the coordinate information of the contour in each cardiac phase. Then, the display controller 7 causes the display 81 to display the newly obtained markers so as to be superimposed on the image in each cardiac phase and additionally causes the display 81 to display the newly obtained wall-motion information.

Figure 5:
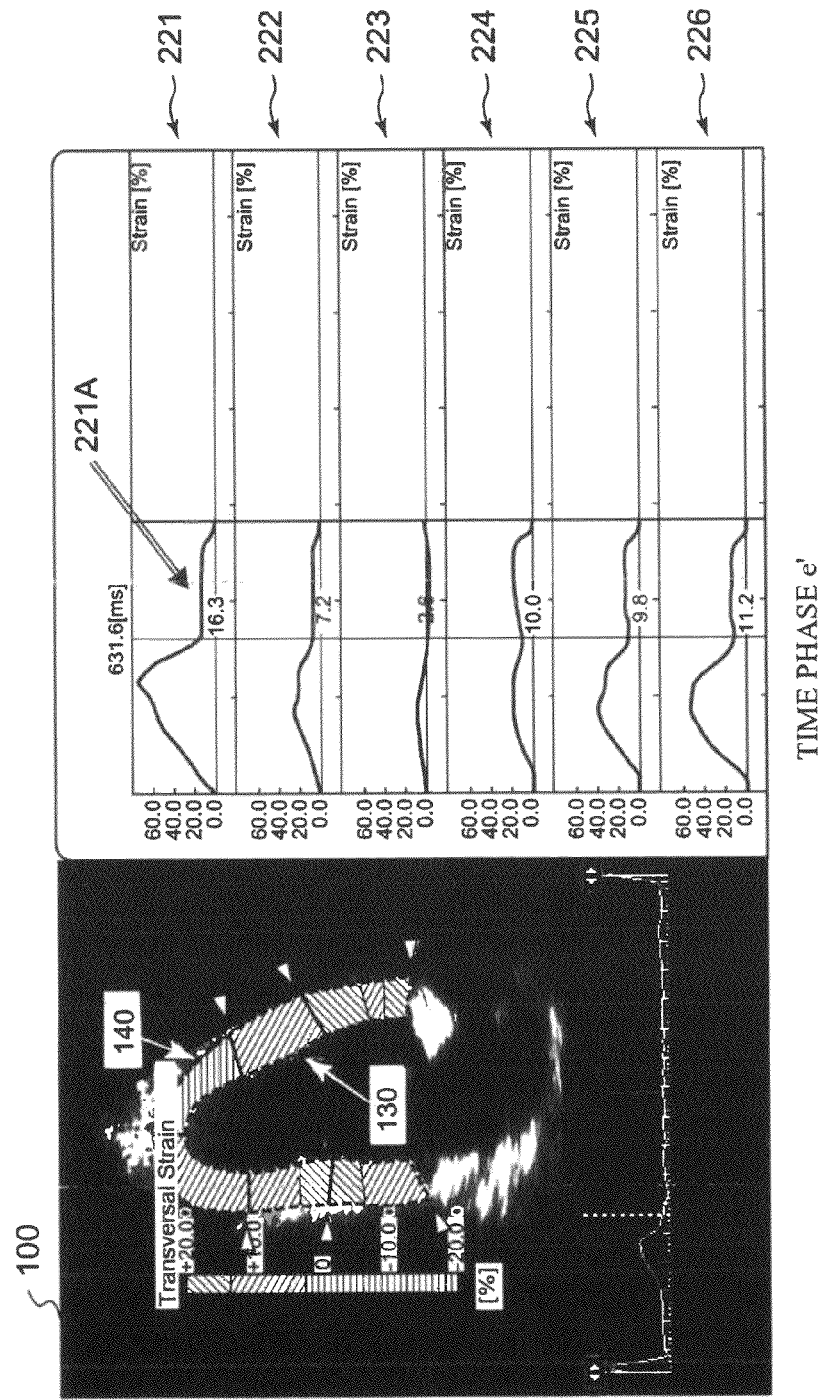
FIG. 5 is a view illustrating an image and wall-motion information acquired by the ultrasound imaging apparatus according to the first embodiment.

The result of the re-tracking process is shown in FIG. 5. As shown in FIG. 5, the display controller 7 causes the display 81 to display newly obtained endocardium marker 130 and epicardium marker 140 so as to be superimposed on the long-axis view 100. Further, the display controller 7 causes the display 81 to display a new graph 221 representing the wall-thickness change rate (Transversal Strain). Consequently, the contour positions are accurately updated by the ST process even in and after the time phase e' (a portion indicated with an arrow 221A). Moreover, by the smoothing process, the waveforms are smoothly connected in the time phase e' (631.6 [msec] in the figure).

Figure 6:
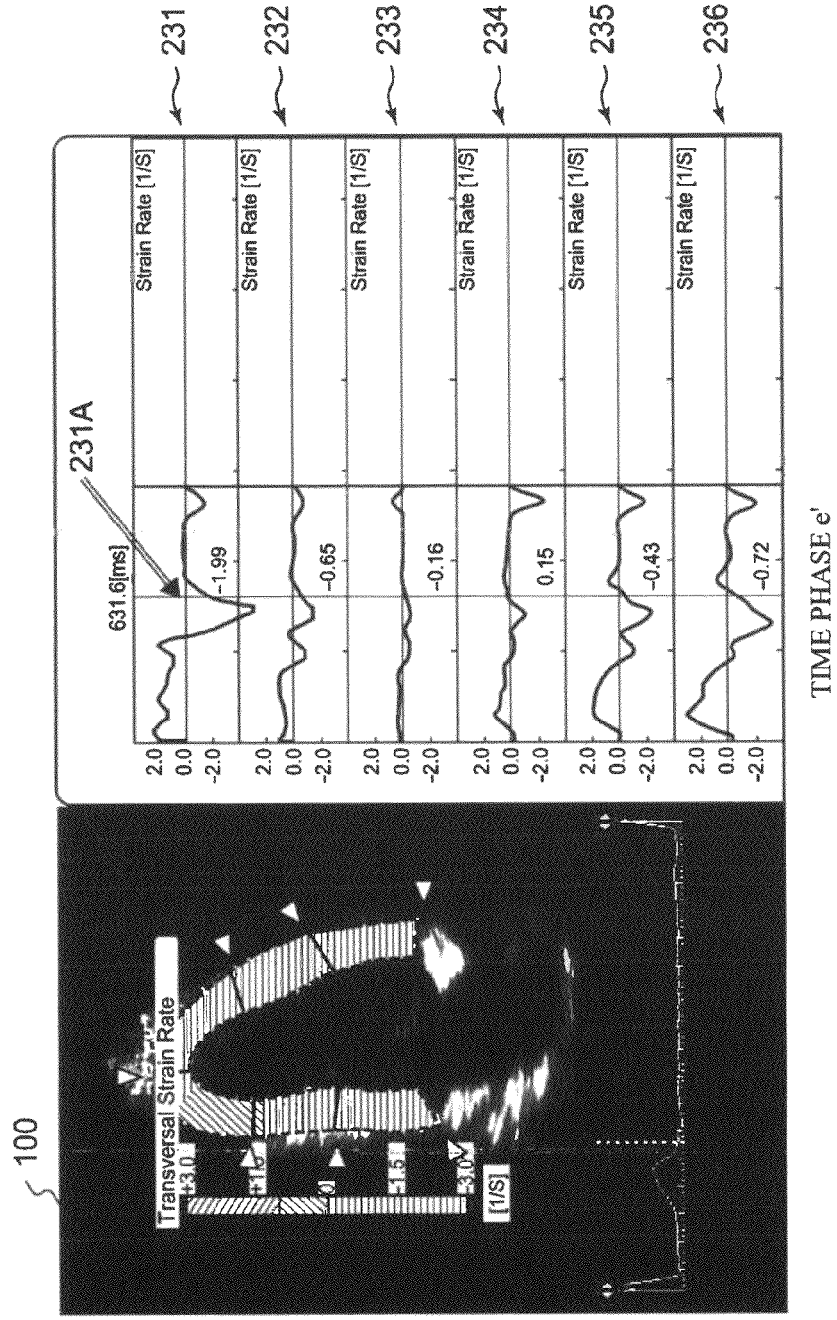
FIG. 6 is a view illustrating an image and wall-motion information acquired by the ultrasound imaging apparatus according to the first embodiment.

Further, FIG. 6 shows graphs 231 through 236 representing the temporal differentiation of the wall thickness change rates (Transversal Strain Rate). The graph 231 is a graph representing the temporal differentiation of the wall-thickness change rate in the region A. As shown in the graph 231, there is no gap among the waveforms in the time phase e' (a portion indicated with an arrow 231A). Thus, it is obvious that the contour positions are smoothly coupled in the time phase e'.

In the description of the first embodiment, it is assumed that a cardiac phase in which tracking of the contour position deviates within one cardiac cycle (from the time phase T0 to the time phase Tend) is only one cardiac phase (the time phase T1). Even if tracking of the contour position deviates in a plurality of cardiac phases, it is possible to correct tracking of the contour position by applying the process according to the first embodiment. If tracking of the contour position deviates in a cardiac phase T1', which is after a lapse of time after the re-tracking process, the re-tracking process can be executed from the cardiac phase T1'. Even if tracking of the contour position deviates in a plurality of cardiac phases, a more accurate tracking result can be obtained in all the time phases within one cardiac cycle by repeating this re-tracking process up to the cardiac phase Tend.

The user interface (UI) 8 includes the display 81 and the operation part 82. The display 81 is composed of a monitor such as a CRT and a liquid crystal display. On the screen thereof, an image, a three-dimensional image, etc., are displayed. The operation part 82 is composed of a keyboard, a mouse, a trackball, a TCS (touch command screen), or the like, and is given various instructions by operations of the operator. Moreover, the controller 9 is connected to each part of the ultrasound imaging apparatus 1 and controls the operation of each part. The user interface (UI) 8 and the controller 9 configure an example of the "region-of-interest setting part" in the present invention.

The image processor 10 includes a not-shown CPU (central processing unit), and a not-shown storage such as a ROM (read-only memory), a RAM (random access memory) and an HDD (hard disk drive). The storage stores an image-processing program for executing the function of the image processor 10. The image-processing program includes a contour-tracking program for executing the function of the contour tracking part 11, a re-tracking program for executing the function of the re-tracking part 12, a position-computing program for executing the function of the position calculator 13, and a marker-generating program for executing the function of the marker generator 14. Then, by execution of the contour-tracking program by the CPU, the contour of the endocardium and the contour of the epicardium in each cardiac phase are obtained. Moreover, by execution of the re-tracking program by the CPU, the contour positions in each cardiac phase in and after an arbitrary cardiac phase are obtained. Moreover, by execution of the position-computing program by the CPU, the contour positions in all time phases are obtained.

Moreover, by execution of the marker-generating program by the CPU, an endocardium marker representing the contour of the endocardium and an epicardium marker representing the contour of the epicardium are generated.

Further, the computing part 20 includes a not-shown CPU, and a not-shown storage such as a ROM, a RAM and an HDD. The storage stores a computing program for executing the function of the computing part 20. The computing program includes a motion-information calculation program for executing the function of the motion-information calculator 21, and a color-determining program for executing the function of the color determining part 22. Then, by execution of the motion-information calculation program by the CPU, wall-motion information in each cardiac phase is obtained. Moreover, by execution of the color-determining program by the CPU, a color associated with the magnitude of the wall-motion information is determined.

Further, the display controller 7 includes a not-shown CPU, and a not-shown storage such as a ROM, a RAM and an HDD. The storage stores a display control program for executing the function of the display controller 7.

Then, by execution of the display control program by the CPU, the display 81 is caused to display an image, a marker, and wall-motion information.
(Ultrasound Image Processing Apparatus)

Further, an ultrasound image processing apparatus may be composed of the storage 6, the display controller 7, the user interface (UI) 8, the image processor 10, and the computing part 20, which are described above. This ultrasound image processing apparatus acquires a plurality of image data (moving image data) acquired at continuous times from an external ultrasound imaging apparatus, and obtains wall-motion information by tracking the contour positions of the endocardium and the epicardium based on the plurality of image data.

As a result of scan of the heart with ultrasound waves by the ultrasound imaging apparatus, the image data is acquired for each cardiac phase. Then, the ultrasound image processing apparatus receives the plurality of image data acquired by the ultrasound imaging apparatus and causes the storage 6 to store the plurality of image data. The image processor 10 of the ultrasound image processing apparatus obtains the position of each of the points composing the two-dimensional contour of endocardium (epicardium) in each cardiac phase, thereby tracking the contour of the endocardium (epicardium). Furthermore, the image processor 10 re-tracks the contour of the endocardium (epicardium) in each cardiac phase in and after the cardiac phase in which an instruction for correction has been given, thereby obtaining the contour positions in the total interval. Then, the computing part 20 of the ultrasound image processing apparatus obtains wall-motion information in each cardiac phase, based on the position of each of the points composing the two-dimensional contour of the endocardium (epicardium) tracked by the image processor 10. Moreover, the computing part 20 determines a color according to the magnitude of the wall-motion information.

Accordingly, as well as the abovementioned ultrasound imaging apparatus 1, the ultrasound image processing apparatus is capable of correcting deviation in tracking of the contour positions by a simple operation and obtaining more accurate contour positions in the whole interval.

Second Embodiment

Next, an ultrasound imaging apparatus according to a second embodiment of the present invention will be described. The above first embodiment describes the case that the ST process is executed once within one heartbeat and tracking of the contour position deviates in a certain time phase (time phase T1). The second embodiment describes a case of executing the ST process for a plurality of heartbeats. Since the configuration of the ultrasound imaging apparatus according to the second embodiment is the same as that of the ultrasound imaging apparatus 1 according to the first embodiment, the operation of the ultrasound imaging apparatus according to the second embodiment will be described.
(Step S01)

First, the operator designates a plurality of heartbeats (from the time phase T0 to the time phase Tend) by using the operation part 82. When the plurality of heartbeats are designated, information representing from the time phase T0 to the time phase Tend is outputted from the user interface (UI) 8 to the image processor 10 and the display controller 7.
(Step S02)

Then, the operator designates the position of an initial contour in an initial time phase in a certain heartbeat by using the operation part 82. More specifically, the display controller 7 reads image data in an initial time phase in a certain heartbeat from the storage 6, and causes the display 81 to display an image based on the image data. For example, when the operator designates the time phase T0 in the first heartbeat as the initial time phase by using the operation part 82, the display controller 7 causes the display 81 to display an image in the time phase T0 of the first heartbeat. Then, the operator designates the position of the initial contour of the endocardium and the position of the initial contour of the epicardium on the image by using the operation part 82.
(Step S03)

Based on the positions of the initial contours designated by the operator, the contour tracking part 11 executes the ST process on the image data acquired in the plurality of heartbeats (between the time phase T0 and the time phase Tend), thereby obtaining the contour position of the endocardium and the contour position of the epicardium in each cardiac phase in the interval between the time phase T0 and the time phase Tend.

Then, the display controller 7 causes the display 81 to display an endocardium marker and an epicardium marker so as to be superimposed on an image in each of the cardiac phases, in the order of the cardiac phases. As in the first embodiment, the operator compares the contour of the endocardium represented on the image in each of the cardiac phases with the position of the endocardium marker, thereby determining the presence of correction of the contour position. Also regarding the epicardium, the operator compares the contour of the epicardium represented on the image in each of the cardiac phases with the position of the epicardium marker, thereby determining the presence of correction of the contour position.
(Step S04)

Then, as in the first embodiment, when the contour position by the ST process deviates from the tracking in the time phase T1, the contour position in the time phase T1 in which it has deviated from the tracking is corrected.
(Step S05)

The re-tracking part 12 executes, with the corrected contour position as the initial contour, the ST process on the image data in each of the cardiac phases acquired between the time phase T1 in which the tracking deviated and the last time phase Tend, thereby obtaining the contour position P1 in each of the cardiac phases between the time phase T1 and the time phase Tend.
(Step S06)

Then, the position calculator 13 connects, in the time phase T1, the contour position P0 in each of the cardiac phases between the time phase T0 and the time phase T1 with the contour position P1 in each of the cardiac phases between the time phase T1 and the time phase Tend, thereby obtaining the contour positions in the total interval. Furthermore, the position calculator 13 smoothes, in the time phase T1, the contour position P0 and the contour position P1 in the time direction, thereby smoothly connecting the contour position P0 with the contour position P1.

According to the operation in the second embodiment, in a case that there is no deviation of tracking within a certain heartbeat but minute errors of the tracking position accumulates in tracking for a plurality of heartbeats and the tracking position largely deviates in a certain cardiac phase within another heartbeat, it is possible to execute the re-tracking process with a time phase in which the tracking position deviates as the time phase T1, and thereby easily obtain a more accurate tracking result.

Further, in the case of executing the ST process on a plurality of heartbeats, even if the tracking deviates in a plurality of cardiac phases, e.g., in the time phase e' of every heartbeat, it is possible to obtain more accurate tracking results in all the cardiac phases of the plurality of heartbeats, by sequentially re-tracking in the time phase e' in which the tracking deviates, as in the first embodiment.

Third Embodiment

Next, an ultrasound imaging apparatus according to a third embodiment of the present invention will be described with reference to FIGS. 7 through 10. FIGS. 7 through 10 are schematic views for illustrating the process performed by the ultrasound imaging apparatus according to the third embodiment. The abovementioned first embodiment and second embodiment describe without particularly limiting the site of the contour to which re-tracking is applied. In the third embodiment, re-tracking is executed only on an area to which a correction has been applied. This makes it possible to reduce the time required for re-tracking. Since the configuration of the ultrasound imaging apparatus according to the third embodiment is the same as that of the ultrasound imaging apparatus 1 according to the first embodiment, the operation of the ultrasound imaging apparatus according to the third embodiment will be described. In FIGS. 7 through 10, a total contour 300 is schematically shown. Furthermore, in FIGS. 7 through 10, the relationship between the total contour position and the position of an area to which a correction has been applied is schematically shown. In the views representing this relationship, the horizontal axis indicates the time and the vertical axis indicates the contour position.
(Step S01 T0 Step S03)

As in the abovementioned first or second embodiment, the operator designates the interval between the time phase T0 and the time phase Tend by using the operation part 82 (Step S01). The operator then designates the position of the initial contour in the initial time phase by using the operation part 82. For example, the operator designates the position of the initial contour of the endocardium and the position of the initial contour of the epicardium on the image in the time phase T0 by using the operation part 82 (Step S02). The contour tracking part 11 executes, based on the positions of the initial contours designated by the operator, the ST process on the image data acquired during the interval between the time phase T0 and the time phase Tend, thereby obtaining the contour position of the endocardium and the contour position of the epicardium in each cardiac phase between the time phase T0 and the time phase Tend (Step S03).
(Step S04)

The display controller 7 then causes the display 81 to display the endocardium marker and the epicardium marker so as to be superimposed on the image in each of the cardiac phases, in the order of the cardiac phases.

Figure 7:
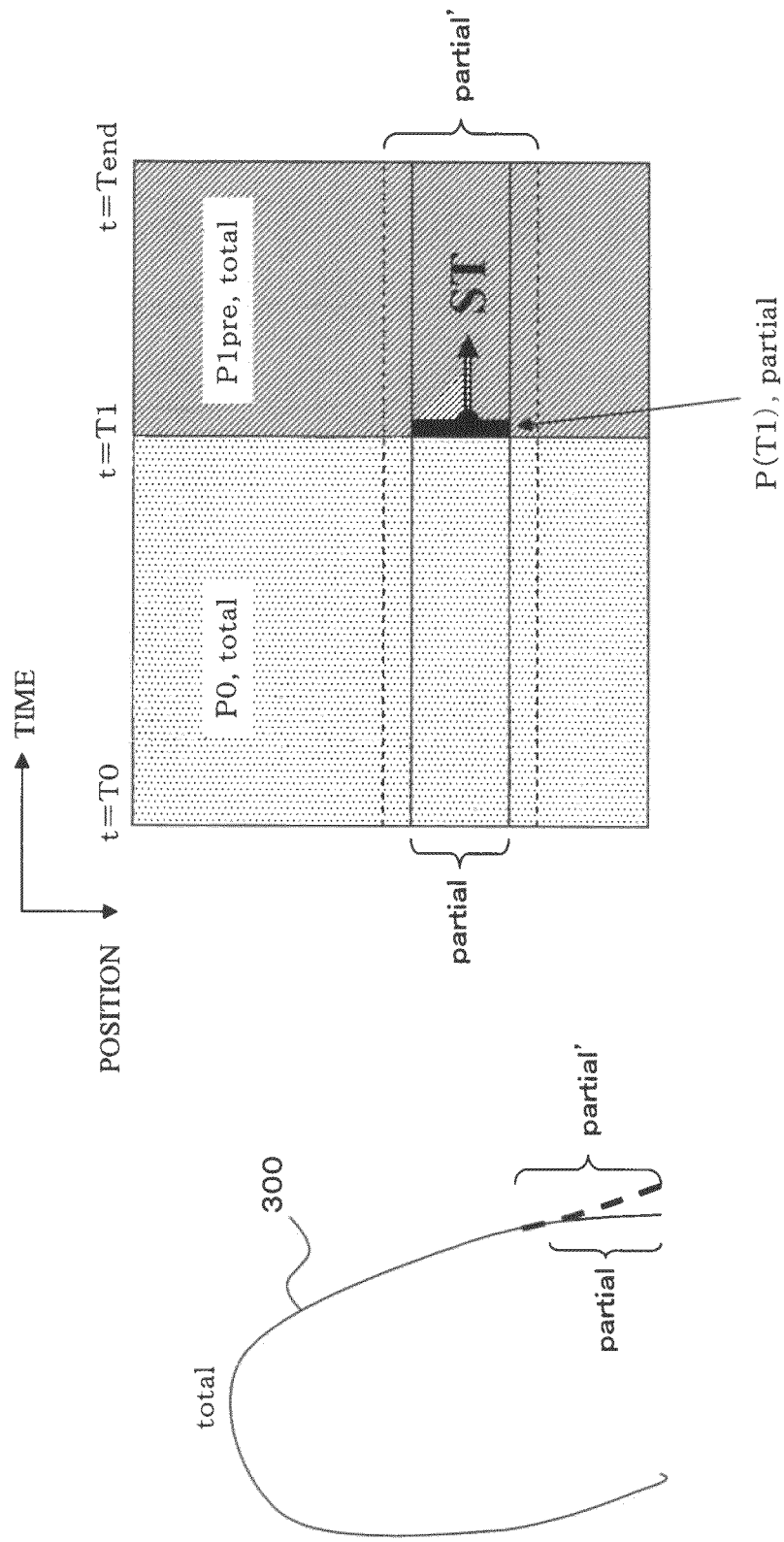
FIG. 7 is a schematic view for describing a process by an ultrasound imaging apparatus according to a third embodiment.

When the contour position by the ST process deviates from tracking in the time phase T1, the contour position by the ST process is corrected in the time phase T1. For example, as shown in FIG. 7, a partial contour (partial), which is a partial region, in the total contour 300 is corrected. When the partial region of the total contour is thus corrected by the operator, position information representing the position of the corrected partial contour is outputted from the user interface (UI) 8 to the image processor 10 via the controller 9.
(Step S05)

The re-tracking part 12 executes the ST process on the image data acquired during the interval between the time phase T1 and the last time phase Tend with the partly corrected partial contour as the initial contour, thereby obtaining the position of the partial contour in each cardiac phase between the time phase T1 and the time phase Tend. For example, as shown in FIG. 7, the re-tracking part 12 executes the ST process only on a partial contour position (P(T1), partial) including a contour corrected in the time phase T1 and a neighborhood region thereof between the time phase T1 and the last time phase Tend with the partial contour position (P(T1), partial) in the time phase T1 as an initial contour, thereby tracking the initial contour.

Consequently, a partial contour position (P1, partial) in each cardiac phase between the time phase T1 and the time phase Tend is updated.

On the other hand, when an instruction for re-tracking is given by the operator, information of a total contour position (P0, total) representing the position of the total contour between the time phase T0 and the time phase T1 and information of a total contour position (P1pre, total) representing the position of the total contour between the time phase T1 and the time phase Tend are outputted from the contour tracking part 11 to the position calculator 13. Then, the position calculator 13 retains the total contour position (P0, total) representing the position of the total contour between the time phase T0 and the time phase T1 and the total contour position (P1pre, total) representing the position of the total contour between the time phase T1 and the time phase Tend.

Figure 8:
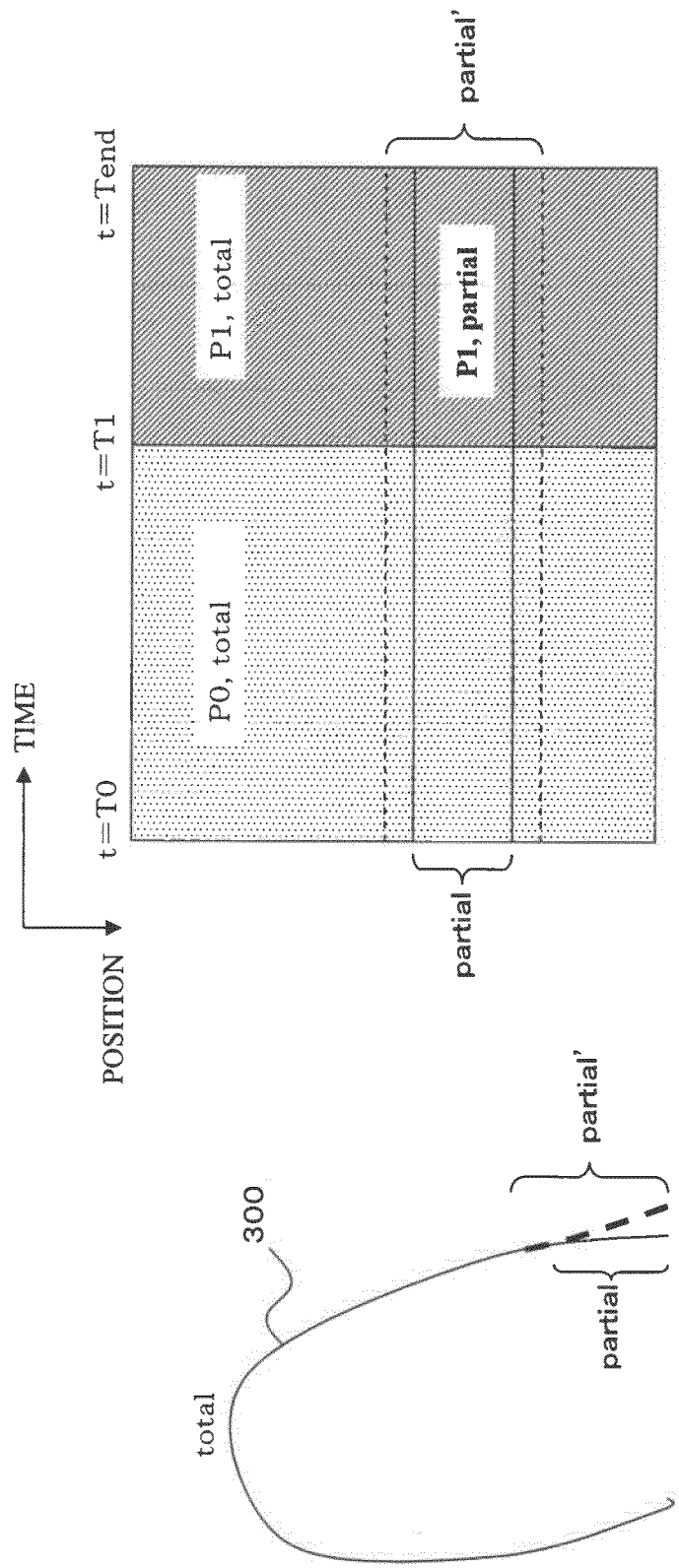
FIG. 8 is a schematic view for describing a process by the ultrasound imaging apparatus according to the third embodiment.

Then, as shown in FIG. 8, the position calculator 13 updates only the partial contour position (P1, partial) of the retained total contour position (P1pre, total), thereby obtaining a total contour position (P1, total) representing the position of the total contour after re-tracking.

(Step S06)

Figure 9:
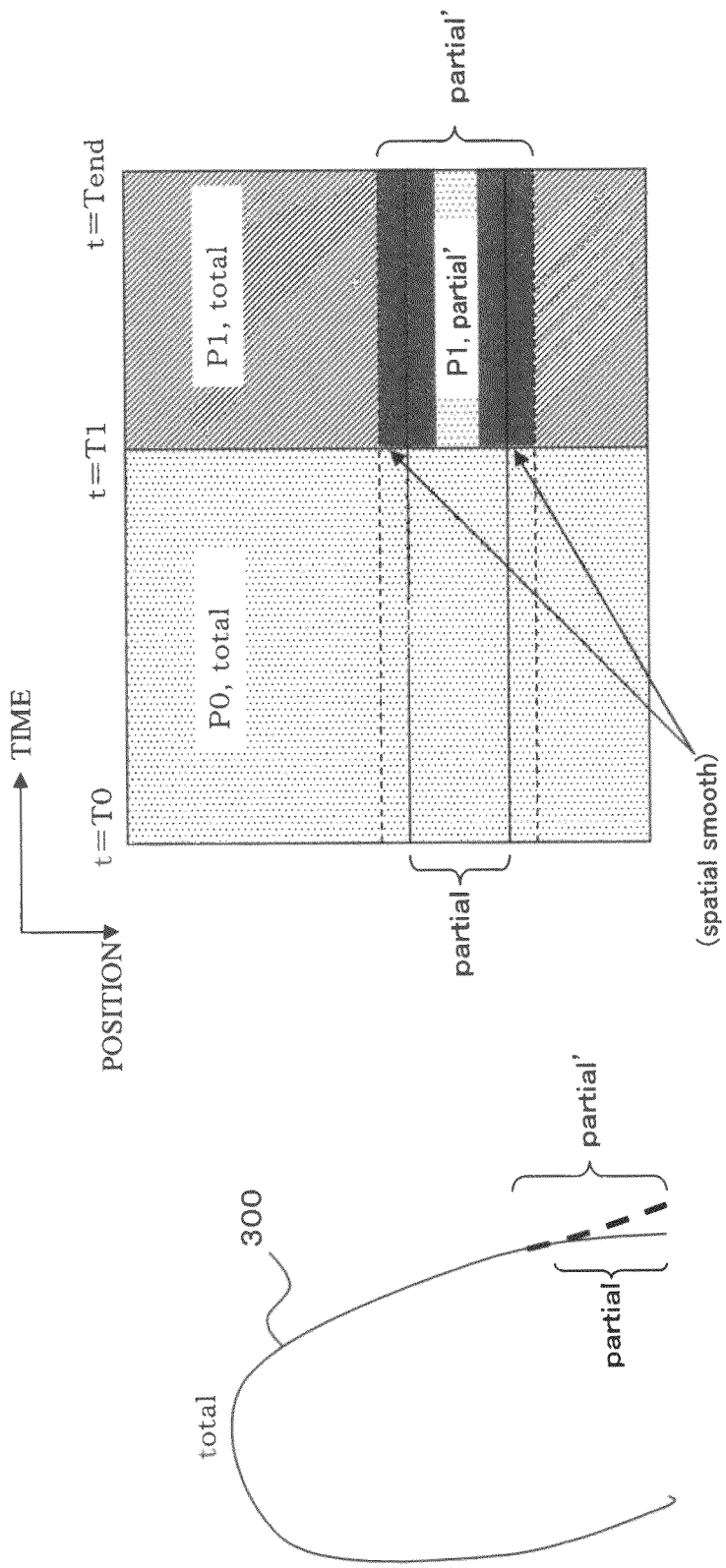
FIG. 9 is a schematic view for describing a process by the ultrasound imaging apparatus according to the third embodiment.

Further, as shown in FIG. 9, the position calculator 13 executes, in the time phase T1, spatial smoothing at a boundary part between the contour position of the total contour and a neighborhood region of the corrected site, thereby connecting the total contour position (P1pre, total) and a partial contour position (P1, partial') so as to be spatially smooth ("spatial smooth" in FIG. 9).

(Step S07)

Figure 10:
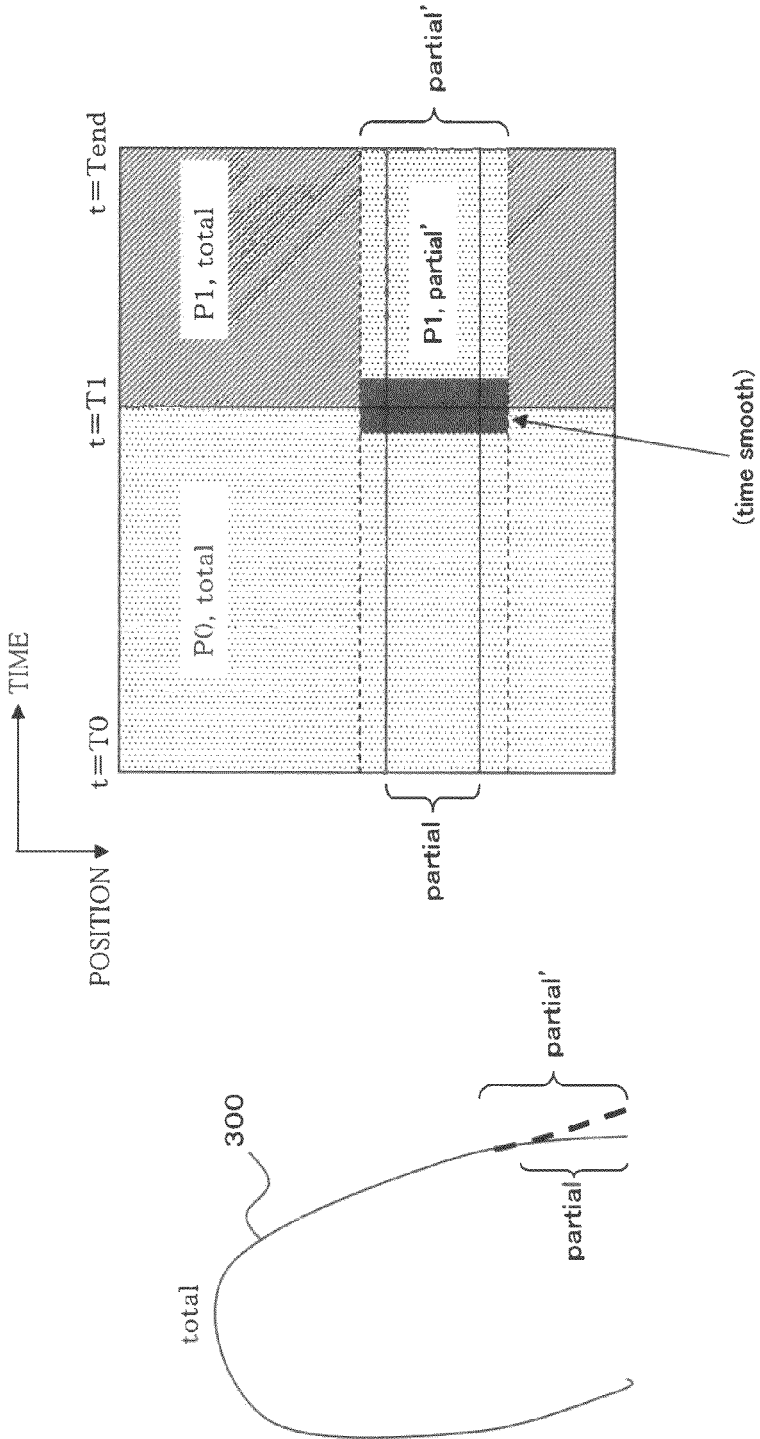
FIG. 10 is a schematic view for describing a process by the ultrasound imaging apparatus according to the third embodiment.

Furthermore, as shown in FIG. 10, the position calculator 13 executes smoothing in the time direction in the time phase T1, thereby smoothly connecting a partial contour position (P0, partial') between the time phase T0 and the time phase T1 and the partial contour position (P1, partial').

Considering broadening by the spatial smoothing in Step S06, it is preferable to use a partial contour position (partial') extended from the partial contour position in Step S05 as a partial contour position subjected to the smoothing.

The tracking by the ST process requires a certain amount of calculation time to estimate a movement vector. On the other hand, it is possible to execute the smoothing in the time direction and the spatial smoothing at relatively higher speeds than the ST process. Therefore, by not re-tracking the total contour but re-tracking only a corrected part and thereafter executing the smoothing as in the third embodiment, it is possible to increase the speed of the re-tracking.

Further, as shown in Step S06, it is preferable to execute the spatial smoothing by the position calculator 13. In the ST process, assuming the spatial continuity of a living body, it is general to execute the smoothing in the spatial direction to exclude change of a contour position that is spatially too precipitous. Therefore, change of the contour position in each site of the total contour is relatively smooth due to the ST process. Moreover, change of the contour position within the partial contour is also relatively smooth due to the ST process. However, regarding the partial contour cut out from the total contour due to correction, a gap of the contour positions is made at the boundary. Thus, in order to reduce this spatial gap, it is preferable to execute the smoothing in the spatial direction in the area where the total contour and the partial contour are connected.

Fourth Embodiment

Figure 11:
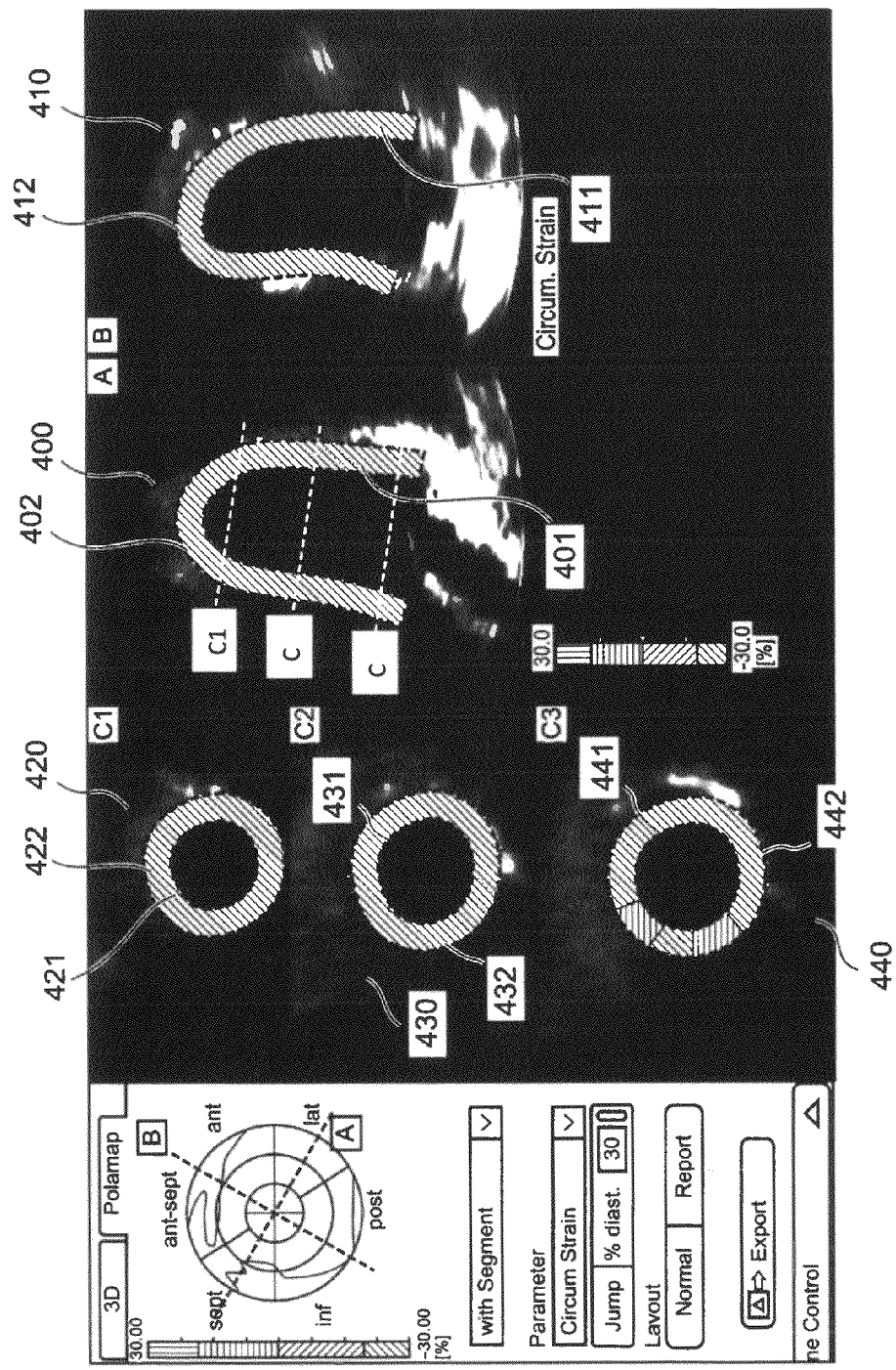
FIG. 11 is a view illustrating an image for describing a process by an ultrasound imaging apparatus according to a fourth embodiment.

Next, an ultrasound imaging apparatus according to a fourth embodiment of the present invention will be described with reference to FIG. 11. FIG. 11 is a view illustrating an image for explaining the process by the ultrasound imaging apparatus according to the fourth embodiment. In the above-mentioned embodiment, two-dimensional moving image data representing the heart is targeted, but the ultrasound imaging apparatus according to the present invention may also target volume moving image data that is three-dimensionally acquired. In other words, the ultrasound imaging apparatus according to the fourth embodiment tracks a three-dimensional contour of the endocardium and a three-dimensional contour of the epicardium based on volume data that is a three-dimensional image, and obtains wall-motion information. Since the configuration of the ultrasound imaging apparatus according to the fourth embodiment is the same as that of the ultrasound imaging apparatus 1 according to the first embodiment, the operation of the ultrasound imaging apparatus according to the fourth embodiment will be described.

Re-tracking according to the fourth embodiment is the same as the tracking according to the first embodiment. However, since three-dimensional image data is targeted, inventiveness is needed for a method of displaying images. A concrete example of the process according to the fourth embodiment will be described below.

In the fourth embodiment, volume data is acquired for each cardiac phase by executing volume scan with the ultrasound probe 2 and the transceiver 3. Then, the image generator 5 executes the MPR process on the volume data, thereby generating MPR image data in an arbitrary cross section.

For example, the image generator 5 executes the MPR process on volume data, thereby obtaining MPR image data of a plurality of different cross sections for each of the cross sections. Then, on an MPR image, the degree of tracking deviation of the contour position is determined, and also the contour position is corrected.

For example, as shown in FIG. 11, the image generator 5 generates a long-axis view 400 (Apical 4 Chamber image) of a long-axis cross section A along the long-axis direction of the heart and a long-axis view 410 of a long-axis cross section B orthogonal to the long-axis cross section A. Furthermore, the image generator 5 generates MPR image data (short-axis view data) of a short-axis cross section (C plane) along a direction (short-axis direction) orthogonal to the long-axis direction. For example, as shown in FIG. 11, the image generator 5 generates a short-axis view 420 of a plane C1 (apical) at a predetermined depth in the long-axis direction. Similarly, the image generator 5 generates a short-axis image 430 of a plane C2 (middle) at a predetermined depth, and generates a short-axis view 440 of a plane C3 (basal) at a predetermined depth. The MPR image data generated by the image generator 5 are stored into the storage 6. Moreover, the planes C1, C2 and C3 may be previously set in the image generator 5, or the operator may designate the planes by using the operation part 82.

With reference to the long-axis view 400 and the long-axis view 410 displayed on the display 81, the operator designates the initial contour of the endocardium and the initial contour of the epicardium on the long-axis view 400 and the long-axis view 410 by using the operation part 82. When the initial contours are thus designated by the operator, coordinate information of the initial contour of the endocardium and the coordinate information of the initial contour of the epicardium on the long-axis cross section A are outputted from the user interface (UI) 8 to the image processor 10. Similarly, coordinate information of the initial contour of the endocardium and the coordinate information of the initial contour of the epicardium on the long-axis cross section B are outputted from the user interface (UI) 8 to the image processor 10.

The contour tracking part 11 spatially interpolates the contour of the endocardium in the circumferential direction, based on coordinate information of the initial contour of the endocardium in the long-axis cross section A and the coordinate information of the initial contour of the endocardium in the long-axis cross section B, thereby obtaining a three-dimensional initial contour position of the endocardium. Similarly, the contour tracking part 11 spatially interpolates the contour of the epicardium in the circumferential direction, based on coordinate information of the initial contour of the epicardium on the long-axis cross section A and coordinate information of the initial contour of the epicardium on the long-axis cross section B, thereby obtaining a three-dimensional initial contour position of the epicardium.

Then, the contour tracking part 11 executes pattern matching by the ST method on the volume data acquired in each cardiac phase with the three-dimensional initial contour of the endocardium as a tracking target, thereby obtaining the position of each of the points composing the three-dimensional contour of the endocardium in each cardiac phase. Similarly, the contour tracking part 11 obtains the position of each of the points composing the three-dimensional contour of the epicardium in each cardiac phase, by the ST method, with the three-dimensional initial contour of the epicardium as a tracking target. Thus, the contour tracking part 11 tracks the three-dimensional contour of the endocardium and the three-dimensional contour of the epicardium.

As in the first embodiment, the motion-information calculator 21 of the computing part 20 obtains wall-motion information in each cardiac phase, based on coordinate information of each of the points composing the three-dimensional contour of the endocardium in each cardiac phase and coordinate information of each of the points composing the three-dimensional contour of the epicardium. As an example, the motion-information calculator 21 obtains wall-motion information in the long-axis cross section A, wall-motion information in the long-axis cross section B, wall-motion information in the plane C1, wall-motion information in the plane C2, and wall-motion information in the plane C3.

Further, the marker generator 14 generates an endocardium marker representing the contour of the endocardium in each cardiac phase and an epicardium marker representing the contour of the epicardium. As an example, the marker generator 14 generates endocardium markers representing the endocardium and epicardium markers representing the epicardium, respectively, in the long-axis cross section A, long-axis cross section B, plane C1, plane C2 and plane C3.

Then, the display controller 7 causes the display 81 to display an MPR image in each cardiac phase, for each cardiac phase. Furthermore, the display controller 7 causes the display 81 to sequentially display the endocardium marker and the epicardium marker in each cardiac phase so as to be superimposed on the MPR image in each cardiac phase.

For example, as shown in FIG. 11, the display controller 7 causes the display 81 to display the long-axis view 400, long-axis view 410, short-axis view 420, short-axis view 430 and short-axis view 440 in each cardiac phase, for each cardiac phase. Moreover, the display controller 7 causes the display 81 to display an endocardium marker 401 and an epicardium marker 402 in each cardiac phase so as to be superimposed on the long-axis view 400.

Similarly, the display controller 7 causes the display 81 to display an endocardium marker 411 and an epicardium marker 412 in each cardiac phase so as to be superimposed on the long-axis view 410. Further, the display controller 7 causes the display 81 to display an endocardium marker 421 and an epicardium marker 422 in each cardiac phase so as to be superimposed on the short-axis view 420. Further, the display controller 7 causes the display 81 to display an endocardium marker 431 and an epicardium marker 432 in each cardiac phase so as to be superimposed on the short-axis view 430.

Furthermore, the display controller 7 causes the display 81 to display an endocardium marker 442 and an epicardium marker 443 in each cardiac phase so as to be superimposed on the short-axis view 440.

Furthermore, as in the abovementioned first embodiment, the display controller 7 assigns a color according to the magnitude of the wall-motion information obtained by the computing part 20 to a region between the endocardium and the epicardium, and causes the display 81 to display it so as to be superimposed on each MPR image.

For example, in a case that the contour position by the ST process deviates from tracking in the time phase e' (time phase T1), correction of the contour position by the ST process is executed in the time phase T1. More specifically, the operator compares the contour represented on the MPR image in the time phase T1 with the contour by the ST process, and corrects the contour position by the ST process. At this moment, the operator corrects the relevant contour site within the MPR image displayed on the display 81 by using the operation part 82.

Then, as in the first embodiment, the re-tracking part 12 executes, the ST process on each of the volume data acquired between the time phase T1 and the last time phase Tend with the corrected contour position as an initial contour, thereby obtaining the contour position in each of the cardiac phases between the time phase T1 and the time phase Tend. Then, the position calculator 13 connects, in the time phase T1, the contour position in each of the cardiac phases between the time phase T0 and the time phase T1 with the contour position in each of the cardiac phases between the time phase T1 and the time phase Tend, thereby obtaining the contour positions in all the time phases. Consequently, the three-dimensional contour position is corrected and tracked.

Further, to the process according to the fourth embodiment, the process according to the second embodiment or the process according to the third embodiment may be applied.

Further, an organ tracked in the first through fourth embodiments described above is not limited to the heart, and may be an arterial vessel such as the carotid artery, which repeats dilation and constriction in synchronization with a cardiac cycle.

What is claimed is:

1. An ultrasound imaging apparatus, comprising: an ultrasonic probe and transceiver configured to scan a periodically moving subject with ultrasound waves to acquire a plurality of ultrasound image data representing the subject;
   a processing circuit configured to set a region of interest in the ultrasound image data acquired in a first time phase, and in time phases after the first time phase, track a position of the region of interest after the first time phase until a second time phase based on ultrasound image data acquired as to generate a first track, wherein the region of interest represents a part of the subject that is in motion during a cardiac cycle,
   wherein the processing circuit is further configured to receive, from a user interface, manual input of a correction instruction of the position of the region of interest in the second time phase, track the corrected position of the region of interest in and after the second time phase based on the received correction instruction and ultrasound image data acquired in and after the second time phase so as to generate a second track, obtain position information of the region of interest in an interval including the first time phase and the second time phase, the interval including a period before the first time phase and a period after the second time phase, by connecting the first track in a first period after the first time phase and before the second time phase to the second track in a second period in and after the obtained second time phase, and obtain, based on the obtained position information of the region of interest, motion information of the tissue included in the region of interest; and
   the ultrasound imaging apparatus further includes a display controller circuit configured to cause a display to display the motion information.

2. The ultrasound imaging apparatus according to claim 1, wherein:
   the processing circuit is further configured to set the region of interest within an interval of one heartbeat unit; and
   the user interface, within the interval of one heartbeat unit, receives input of the correction instruction of the position of the region of interest in the second time phase within the interval, and the processing circuit tracks the corrected position of the region of interest in and after the second time phase.

3. The ultrasound imaging apparatus according to claim 1, wherein:
the processing circuit is further configured to set the region of interest within an interval of two heartbeats or more; and
the user interface, within the interval of two heartbeats or more receives input of the correction instruction of the position of the region of interest in the second time phase within the interval, and the processing circuit tracks the corrected position of the region of interest in and after the second time phase.

4. The ultrasound imaging apparatus according to claim 1, wherein:
for the position information of the region of interest in the first period in and before the second time phase and the position information of the region of interest in the second period in and after the second time phase, the processing circuit is further configured to smooth the position of the region of interest at a neighborhood time of the second time phase.

5. The ultrasound imaging apparatus according to claim 1, wherein:
the user interface is configured to receive input of a correction instruction of a position of a partial region of the region of interest in the second time phase, and the processing circuit is further configured to track the corrected position of the partial region in and after the second time phase based on the ultrasound image data acquired in and after the second time phase; and
the processing circuit is further configured to obtain the position information of the region of interest, based on position information of a region other than the partial region and the obtained position information of the partial region.

6. The ultrasound imaging apparatus according to claim 5, wherein:
the processing circuit is further configured to smooth, in the neighborhood of the partial region, the position of the region other than the partial region and the position of the partial region.

7. The ultrasound imaging apparatus according to claim 1, wherein:
the ultrasonic probe and transceiver are further configured to acquire a plurality of three-dimensional image data as the ultrasound image data;
the processing circuit is further configured to set the region of interest in the three-dimensional image data acquired in the first time phase;
in time phases after the first time phase, the processing circuit is further configured to track a position of the region of interest until the second time phase based on three-dimensional image data acquired so as to generate the first track;
the processing circuit is further configured to track the corrected position of the region of interest in and after the second time phase based on the correction instruction input by the user interface and the three-dimensional image data acquired in and after the second time phase so as to generate the second track; and
the processing circuit is further configured to obtain the position information of the region of interest in the interval including the first time phase and the second time phase, by connecting the first track in the first period after the first time phase and before the second time phase to the second track in the second period in and after the obtained second time phase.

8. A method for processing an ultrasound image, comprising:
scanning a periodically moving subject with ultrasound waves to acquire a plurality of ultrasound image data representing the subject;
setting a region of interest in the ultrasound image data acquired in a first time phase, wherein the region of interest represents a part of the subject that is in motion during a cardiac cycle;
tracking, in time phases after the first time phase, a position of the region of interest after the first time phase until a second time phase based on ultrasound image data acquired to generate a first track;
manually input of a correction instruction of the position of the region of interest in the second time phase;
tracking, by a processing circuit, the corrected position of the region of interest in and after the second time phase based on the received correction instruction and ultrasound image data acquired in and after the second time phase so as to generate a second track;
obtaining, by connecting the first track in a first period after the first time phase and before the second time phase to the second track in a second period in and after the second time phase obtained in the second tracking step, position information of the region of interest in an interval including the first time phase and the second time phase, the interval including a period before the first time phase and a period after the second time phase;
obtaining, based on the position information of the region of interest in the interval including the first time phase and the second time phase, motion information of the tissue included in the region of interest; and
displaying the motion information.

9. The method for processing an ultrasound image according to claim 8, wherein:
the region of interest is set within an interval of one heartbeat unit; and
within the interval of one heartbeat unit, the correction instruction of the position of the region of interest is received in the second time phase within the interval, and the corrected position of the region of interest in and after the second time phase is tracked.

10. The method for processing an ultrasound image according to claim 8, wherein:
the region of interest is set within an interval of two heartbeats or more; and
within the interval of two heartbeats or more, the correction instruction of the position of the region of interest is received in the second time phase within the interval, and the corrected position of the region of interest in and after the second time phase is tracked.

11. The method for processing an ultrasound image according to claim 8, wherein:
for the position information of the region of interest in the first period in and before the second time phase and the position information of the region of interest in the second period in and after the second time phase, the position of the region of interest is smoothed in a neighborhood time of the second time phase.

12. The method for processing an ultrasound image according to claim 8, wherein:
a correction instruction of a position of a partial region of interest is received in the second time phase, and the corrected position of the partial region in and after the second time phase is tracked based on the ultrasound image data acquired in and after the second time phase; and the position information of the region of interest is obtained based on position information of the region other than the partial region and position information of the part of the region obtained by the tracking.

13. The method for processing an ultrasound image according to claim 12, wherein:

in the neighborhood of the partial region, the position of the region other than the partial region and the position of the partial region is smoothed.

14. The method for processing an ultrasound image according to claim 8, wherein:

a plurality of three-dimensional image data are acquired as the ultrasound image data;

the region of interest is set in the three-dimensional image data acquired in the first time phase;

in time phases after the first time phase, the position of the region of interest is tracked after the first time phase until the second time phase based on the three-dimensional image data acquired to generate the first track;

the corrected position of the region of interest in and after the second time phase is tracked based on the correction instruction and the three-dimensional image data acquired in and after the second time phase so as to generate the second track; and by connecting the first track in the first period after the first time phase and before the second time phase to the second track in the second period in and after the second time phase obtained in the second tracking step, position information of the region of interest in the interval including the first time phase and the second time phase is obtained.

* * * * *